US012344899B2

(12) United States Patent
Schroeder et al.

(10) Patent No.: US 12,344,899 B2
(45) Date of Patent: Jul. 1, 2025

(54) COMPOSITIONS AND METHODS FOR THERAPEUTICS PRESCREENING

(71) Applicant: TECHNION RESEARCH & DEVELOPMENT FOUNDATION LIMITED, Haifa (IL)

(72) Inventors: Avi Schroeder, Binyamina (IL); Zvi Yaari, Kiryat Ata (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 243 days.

(21) Appl. No.: 17/079,959

(22) Filed: Oct. 26, 2020

(65) Prior Publication Data

US 2021/0040568 A1 Feb. 11, 2021

Related U.S. Application Data

(63) Continuation of application No. 15/503,437, filed as application No. PCT/IL2015/050826 on Aug. 13, 2015, now Pat. No. 10,815,530.

(30) Foreign Application Priority Data

Aug. 14, 2014 (GB) ..................................... 1414464

(51) Int. Cl.
    *A61P 43/00* (2006.01)
    *A61K 49/00* (2006.01)
    *C12Q 1/6886* (2018.01)

(52) U.S. Cl.
    CPC ........ *C12Q 1/6886* (2013.01); *A61K 49/0004* (2013.01); *A61K 49/0017* (2013.01); *A61K 49/0084* (2013.01); *C12Q 2600/136* (2013.01)

(58) Field of Classification Search
    None
    See application file for complete search history.

(56) References Cited

U.S. PATENT DOCUMENTS

| | | | |
|---|---|---|---|
| 4,897,355 | A | 1/1990 | Eppstein et al. |
| 5,171,678 | A | 12/1992 | Behr et al. |
| 5,334,761 | A | 8/1994 | Gebeyehu et al. |
| 5,744,335 | A | 4/1998 | Wolff et al. |
| 5,885,613 | A | 3/1999 | Holland et al. |
| 6,541,462 | B1 | 4/2003 | Modrak |
| 8,895,072 | B2 | 11/2014 | Yan et al. |
| 2003/0039955 | A1 | 2/2003 | Feng et al. |
| 2010/0233251 | A1 | 9/2010 | Von Andrian et al. |
| 2011/0081362 | A1* | 4/2011 | Elledge .................. A61P 35/00 514/249 |
| 2013/0260447 | A1 | 10/2013 | Link |
| 2013/0274117 | A1* | 10/2013 | Church ................ C12Q 1/6806 435/6.12 |
| 2014/0205543 | A1 | 7/2014 | Penate-Medina et al. |
| 2014/0273246 | A1 | 9/2014 | Bisso et al. |

FOREIGN PATENT DOCUMENTS

| | | |
|---|---|---|
| WO | 2005121348 A1 | 12/2005 |
| WO | 2010042877 A1 | 4/2010 |
| WO | 2010053572 A2 | 5/2010 |
| WO | 2012071559 A2 | 5/2012 |
| WO | 2014083205 A1 | 6/2014 |

OTHER PUBLICATIONS

Alemany et al (Gene Therapy 8:1347-53) (Year: 2001).*
Dodds et al (1998 Gene Therapy 5:542-51). (Year: 1998).*
Mannino et al (Biotechniques 6:682-90) (Year: 1988).*
Felgner et al (Nature 337:387-8) (Year: 1989).*
Sarit S. Agasti et al: "Photocleavable DNA Barcode-Antibody Conjugates Allow Sensitive and Multiplexed Protein Analysis in Single Cells", Journal of the American Chemical Society, 2012, vol. 134, pp. 18499-18502.
V. Budker et al: "Protein/Amphipathic Polyamine Complexes Enable Highly Efficient Transfection with Minimal Toxicity", BioTechniques vol. 23, pp. 139-147, Jul. 1997.
Daryl C. Drummond: "Optimizing Liposomes for Delivery of Chemotherapeutic Agents to Solid Tumors", The American Society for Pharmacology and Experimental Therapeutics, vol. 51, No. 4, pp. 691-743, 1999.
Xiang Gao et al: "A Novel Cationic Liposome Reagent for Efficient Transfection of Mammalian Cells", Biochemical and Biophysical Research Communications, vol. 179, No. 1, Aug. 30, 1991, pp. 280-285.
James Heyes et al: "Cationic lipid saturation influences intracellular delivery of encapsulated nucleic acids", Journal of Controlled Release vol. 107, 2005, pp. 276-287.
Andreas Jahn et al: "Microfluidic Directed Formation of Liposomes of Controlled Size", American Chemical Society, Langmuir, Apr. 24, 2007, vol. 23, pp. 6289-6293.
Alexander L. Klibanov: "Amphipathic polyethyleneglycols effectively prolong the circulation time of liposomes", Federation of European Biochemical Societies, vol. 268, No. 1, pp. 235-237, Jul. 1990.
Dan D. Lasic et al: "Gelation of liposome interior, A novel method for drug encapsulation", Federation of European Bioclaemical Societies, vol. 312, No. 2,3, pp. 255-258, Nov. 1992.
Dan D. Lasic: "Novel applications of liposomes", Trends in Biotechnology, vol. 16, pp. 307-321, Jul. 1998.
David V. Morrissey et al: "Potent and persistent in vivo anti-HBV activity of chemically modified siRNAs", Nature Biotechnology, vol. 23, No. 8, Aug. 2005, pp. 1002-1007.
Kim J. Png et al: "A microRNA regulon that mediates endothelial recruitment and metastasis by cancer cells", Nature vol. 481, pp. 190-194, Jan. 12, 2012.

(Continued)

*Primary Examiner* — Christopher M Gross
(74) *Attorney, Agent, or Firm* — The Roy Gross Law Firm, LLC; Roy D. Gross

(57) ABSTRACT

A theranostic composition and method for determining the cell-specific potency of drugs is provided. Further, compositions and methods useful for studying the therapeutic profile of one or more drugs within a cell microenvironment, including but not limited to a tumor, are provided.

20 Claims, 8 Drawing Sheets

(56) References Cited

OTHER PUBLICATIONS

Steven A. Rosenberg: Cancer: Principles and Practice of Oncology, 7th Edition, Devita et al, Lippincott Williams & Wilkins, 2005, Chapters 15.
Samuel Hellman: Cancer: Principles and Practice of Oncology, 7th Edition, Devita et al, Lippincott Williams & Wilkins, 2005, Chapters 16.
Edward Chu et al: Cancer: Principles and Practice of Oncology, 7th Edition, Devita et al, Lippincott Williams & Wilkins, 2005, Chapters 17.
Douglas R. Lowy et al: Cancer: Principles and Practice of Oncology, 7th Edition, Devita et al, Lippincott Williams & Wilkins, 2005, Chapters 63.
Avi Schroeder et al: "Controlling Liposomal Drug Release with Low Frequency Ultrasound: Mechanism and Feasibility", Langmuir, vol. 23, No. 7, 2007, pp. 4019-4025.
Avi Schroeder et al: "Remotely-activated protein-producing nanoparticles", Nano Letters, vol. 12, No. 6, pp. 2685-2689, Jun. 13, 2012.
Sean C. Semple et al: "Rational design of cationic lipids for siRNA delivery", Nature Biotechnology, vol. 28, No. 2, Feb. 2010, pp. 172-178.
Andrew M. Smith et al: "Quantitative phenotyping via deep barcode sequencing", Genome Research, vol. 19, pp. 1836-1842, 2009.
Adeeti V. Ullal: "Cancer cell profiling by barcoding allows multiplexed protein analysis in fine needle aspirates", Science Translational Medicine, vol. 6, No. 219, Jan. 15, 2014, pp. 1-22.
Rui Zhang et al: "Annexin A5-Conjugated Polymeric Micelles for Dual SPECT and Optical Detection of Apoptosis", Journal of Nuclear Medicine, vol. 52, No. 6, pp. 958-964, Jun. 2011.
International Search Report of PCT/IL2015/050826 Completed Jan. 14, 2016; Mailed Jan. 27, 2016 4 Pages.
Written Opinion of PCT/IL2015/050826 Completed Jan. 14, 2016; Mailed Jan. 27, 2016 7 Pages.
Madeleine S. Bloch et al: "Labeling Milk along Its Production Chain with DNA Encapsulated in Silica", Journal of Agricultural and Food Chemistry, Oct. 29, 2014, vol. 62, No. 43, pp. 10615-10620.
Paul Igor Costea et al: "TagGD: Fast and Accurate Software for DNA Tag Generation and Demultiplexing", PLoS ONE, vol. 8, No. 3, e57521.
Glenn K. Fu et al: "Molecular indexing enables quantitative targeted RNA sequencing and reveals poor efficiencies in standard library preparations", PNAS, Feb. 4, 2014, vol. 111, No. 5, pp. 1891-1896.
Wooram Lee et al: "Endogenous Protein "Barcode" for Data Validation and Normalization in Quantitative MS Analysis", Analytical Chemistry, 2014, vol. 86, pp. 6379-6386.
Xiao Li et al: "Controlled Fabrication of Fluorescent Barcode Nanorods", ACS Nano, 2010, vol. 4, No. 8, pp. 4350-4360.
Daniela Paunescu et al: "Protection and Deprotection of DNA-High-Temperature Stability of Nucleic Acid Barcodes for Polymer Labeling", Angewandte Chemie International Edition, 2013, vol. 52, No. 15, pp. 4269-4272.
Linchen Wang et al: "Molecular Barcodes: Information Transmission via Persistent Chemical Tags", 2015 IEEE International Conference on Communications (ICC), Jun. 8, 2015, pp. 1-6.
Madaswamy S. Muthu et al: "Theranostic liposomes for cancer diagnosis and treatment: current development and pre-clinical success", Expert Opinion on Drug Delivery, Feb. 2013, vol. 10, No. 2, pp. 151-155.
Sander W. Zielhuis et al: "Lanthanide-Loaded Liposomes for Multimodality Imaging and Therapy", Cancer Biotherapy & Radiopharmaceuticals, Oct. 2006, vol. 21, No. 5, 2006, pp. 520-527.
Zvi Yaari et al: "Theranostic barcoded nanoparticles for personalized cancer medicine", Nature Communications, Nov. 10, 2016, vol. 7, article 13325, pp. 1-10.
Dvir et al. (Nanoparticles for targeting the infarcted heart. Nano Lett. Oct. 12, 2011; 11(10): 4411-4414).
Sahay et al. (Efficiency of siRNA delivery by lipid nanoparticles is limited by endocytic recycling. Nature Biotechnology 31 (7) 213: 653-661 ).

* cited by examiner

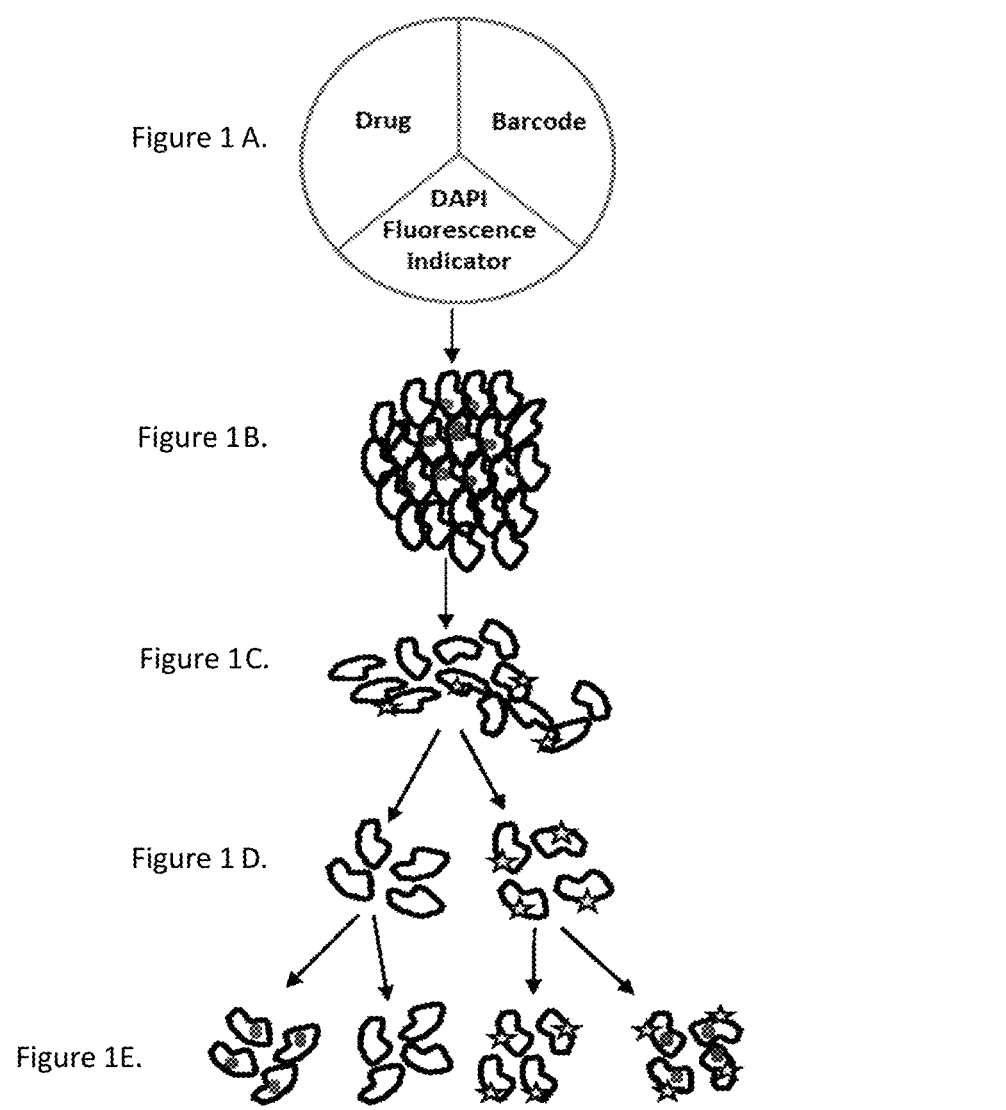
Figure 1 A.
Figure 1B.
Figure 1C.
Figure 1 D.
Figure 1E.
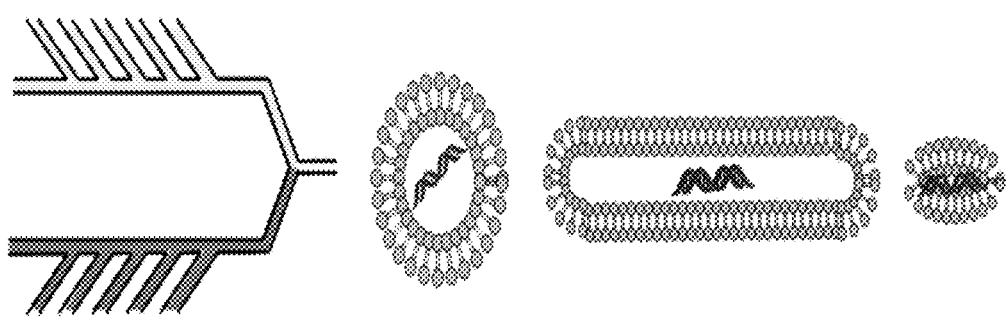
Figure 2

COMPOSITIONS AND METHODS FOR THERAPEUTICS PRESCREENING

CROSS REFERENCE TO RELATED APPLICATIONS

This application is a continuation of U.S. patent application Ser. No. 15/503,437 filed on Feb. 13, 2017, which is a national phase of PCT Patent Application No. PCT/IL2015/050826 having International filing date of Aug. 13, 2015, which claims the benefit of priority of GB Patent Application No. 1414464.6 filed on Aug. 14, 2014. The contents of the above applications are all incorporated by reference as if fully set forth herein in their entirety.

FIELD OF INVENTION

The present invention is directed to; inter alia, compositions and assays useful in predicting personalized therapeutic potency and activity of therapeutic agents.

BACKGROUND OF THE INVENTION

Patients respond differently to medication; the success of a treatment depends greatly on selecting the right drug for each patient. 'Personalized Medicines' are aimed at addressing each patient's unique disease presentation. Diseases and disorders which require personalized medicine include malignant diseases, inflammatory diseases and neurodegenerative disease.

Cancer, as a non-limiting example, has a low actual response rate to medicines in the clinic. For example, less than 60% of breast, esophagus, colon or stomach-cancer patients respond to therapy; statistics decrease to less than 30% in patients with lung, melanoma, pancreatic, liver or recurrent ovarian cancers. Thus, selecting for the proper therapeutic, that will address each patient's unique disease presentation, can significantly improve the treatment outcome.

Prescreening drugs for their patient-specific anticancer activity is a challenging task. Under existing approaches which attempt to predict whether a cancer treatment will be successful, biopsies are taken from a patient's tumor after a short chemotherapeutic cycle, and examined histologically for tumor response. Imaging technologies enabled tracking a treatment's effect on tumor regression/progression, vasculature proliferation and metabolic activity at real time. To prescreen multiple drugs and drug combinations for their anticancer activity, ex vivo and in vitro assays were developed. These assays are based on tumor tissue that is biopsied from the patient and then either expanded in vitro or implanted into immune-deficient mice, in vivo.

The cell culture approach has not proven effective in predicting the therapeutic outcome due to the lacking of a heterogeneous, multi-cellular, tumor microenvironment. The second approach has proven to be somewhat effective; however, it takes 7-12 months to generate a sufficient number of mice for the screen. Therefore, only patients with mild and non-progressive tumors can be selected for this assay.

Genetic information and patient-specific biomarkers have helped advance personalized medicine. However, nearly 50% of patients still are mismatched with non-effective treatments, to then be categorized 'non responders'.

Nanotechnologies possess great promise for treating cancer, including, tumor-specific bio-distribution, increased intracellular uptake, and the ability to carry water soluble and insoluble drugs. Nanoparticles also have the ability to concomitantly carry a therapeutic cargo together with contrast agents for imaging antitumor activity in situ (i.e., theranostics) (Zhang, R. et al. 2011, *J Nucl Med* 52, 958-964).

There is an unmet need for compositions and methods for studying personalized therapeutic potency and activity of chemical and biological agents.

SUMMARY OF THE INVENTION

The present invention provides compositions and methods useful for predicting and determining the response of a subject afflicted with a disease to a therapeutic agent or combinations of therapeutic agents.

The present invention presents for the first time a personalized approach enabling simultaneous screening of multiple therapeutic agents, for their patient specific potency, with single-cell resolution. Thereby, the compositions and methods disclosed herein, grant physicians a new handle for selecting drugs tailored for a single patient.

In one aspect, the present invention provides a composition comprising at least one carrier, said at least one carrier comprises:
 (a) a single-cell therapeutically effective amount of at least one therapeutic agent; and
 (b) one or more barcodes uniquely identifying the at least one therapeutic agent of (a).

In some embodiments, the composition comprises a plurality types of carriers, wherein each type of carrier independently comprises:
 (a) a single-cell therapeutically effective amount of at least one therapeutic agent; and
 (b) one or more barcodes uniquely identifying the at least one therapeutic agent of (a).

In some embodiments, said plurality of types of carriers is 1-5000 types of carriers. In some embodiments, said plurality of types of carriers is 1-4000 types of carriers. In some embodiments, said plurality of types of carriers is 1-2000 types of carriers. In some embodiments, said plurality of types of carriers is 1-500 types of carriers. In other embodiments, said plurality of types of carriers is 1-200 types of carriers. In other embodiments, said plurality of types of carriers is 1-10 types of carriers. In other embodiments, said plurality of types of carriers is 1-5 types of carriers. In other embodiments, said plurality of types of carriers is 1-4 types of carriers.

In another embodiment, the composition further comprises at least one control carrier, said control carrier is devoid of a therapeutic agent and comprises one or more barcodes (e.g., a nucleic acid molecule) uniquely identifying said control carrier.

In some embodiments, said therapeutically effective amount is substantially a single-cell therapeutically effective amount. In another embodiment, said therapeutically effective amount is sufficient for modulating the state of a single cell. In another embodiment, said modulating the state of a single cell is selected from: modulating cell proliferation, modulating cell death, modulating cell drug resistance and modulating cell function, activity or physiology. In embodiments wherein said at least one therapeutic agent cannot cross the cell membrane, higher concentration of said therapeutically effective amount may be used.

In another embodiment, said barcode is one or more nucleic acid molecule uniquely identifying said control carrier. In another embodiment, said nucleic acid molecule is 5-1000 nucleotides in length. In another embodiment, said nucleic acid molecule is 5-500 nucleotides in length. In another embodiment, said nucleic acid molecule is 5-400 nucleotides in length. In another embodiment, said nucleic acid molecule is 5-300 nucleotides in length. In another embodiment, said nucleic acid molecule is 5-250 nucleotides in length. In another embodiment, said nucleic acid molecule is 15-200 nucleotides in length.

In another embodiment, said nucleic acid molecule comprises a sequence which is not substantially identical or complementary to said cell's nucleic acid. In another embodiment, said nucleic acid molecule does not enter the cell's nuclei. In another embodiment, said nucleic acid molecule is devoid of a component capable of entering a cell's nuclei (such as a nuclear localization signal (NLS) or nuclei transporter).

In another embodiment, said barcode is selected from the group consisting of: a rare earth element, a fluorophore, a chromophore, a chemilluminescent molecule, a magnetic particle, a dye, and a radioactive isotope. In another embodiment, said barcode is a rare earth element. In another embodiment, said rare earth element is a lanthanide.

In another embodiment, said at least one carrier has a diameter of at most 250 nm (nanometers). In another embodiment, said at least one carrier has a diameter of at least 50 nm. In another embodiment, said at least one carrier is a lipid-based particle. In another embodiment, said at least one carrier is selected from a liposome and a micelle. In another embodiment, said at least one carrier is complexed with the therapeutic agent such as a polymeric nanoparticle, a nanogel, a metallic nanoparticle (including but not limited to a gold or iron oxide nanoparticle), carbon nanotube, a layer by layer particle and sol-gel ceramic particles. In another embodiment, said at least one carrier comprises polyethylene glycol (PEG).

In another embodiment, there is provided a composition comprising a plurality of carriers independently comprising at least one therapeutic agent and a nucleic acid molecule uniquely identifying said at least one therapeutic agent. In another embodiment, said composition is formulated for systemic administration. In another embodiment, said composition is formulated for intratumoral administration.

In another embodiment, said at least one carrier further comprising a tag (e.g., a tracer). In another embodiment, said tag is selected from the group consisting of a fluorophore, a chromophore, a chemilluminescent molecule, a magnetic particle or a dye, a metal, a rare earth and a radioactive isotope. In some embodiments, said tag is useful for screening and/or detecting cells successfully targeted by said carrier. In some embodiments, said tag is further useful for detecting the activity of said therapeutic agent.

According to another aspect, there is provided a method for predicting the response of a subject afflicted with a disease to a therapeutic agent, the method comprising the steps of:
(a) administering to the subject a composition comprising a plurality of types of carriers, each type of carrier independently comprises a single-cell therapeutically effective amount of at least one therapeutic agent and one or more barcodes (nucleic acid molecules) uniquely identifying said at least one therapeutic agent;
(b) obtaining a sample comprising cells from said subject; and
(c) identifying, in cells comprising 1-5 types of carriers, the efficacy of said at least one therapeutic agent by the unique barcode;
thereby predicting the response of a subject afflicted with a disease to a therapeutic agent.

In some embodiments, said subject is afflicted with cancer. In some embodiments, said administration is intravenous injection and said composition comprises 1-200 carries per a single cell of a tumor of said subject. In some embodiments, said administration is intratumoral injection, and said composition comprises 1-20 carries per a single cell of a tumor of said subject.

In some embodiments, said obtaining is performed within a time frame of 24-72 hours following administration of said composition. In some embodiments, said obtaining is performed within a time frame of 24-48 hours following administration of said composition.

In another embodiment, said method further comprises a step of sequencing said nucleic acid molecule. In another embodiment, said method further comprises a step of amplifying said nucleic acid molecule.

In another embodiment, said sample is disassembled into a single-cell suspension prior to step (c).

In another embodiment, said at least one carrier of said composition further comprises at least one tag. In another embodiment, said cells of said sample are sorted using a method selected from the group consisting of: FACS, magnetic bead sorting, enzyme-linked immunosorbent assay (ELISA), microfluidic based sorting, cell-tension based sorting and the like.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-E. A schematic illustration of a non-limiting example for predicting the potency of anticancer therapeutics inside the patient's tumor. (A) Fabrication of nanoparticles containing a drug, a DNA barcode, and a fluorescent dye. (B) A cocktail of nanoparticles, containing different drugs is administered to a subject at an extremely low dose. (C) 48 hr later, a core biopsy is taken from the tumor, and dissociated into a single-cell suspension. (D) The suspension is sorted (e.g., by FACS) based on nanoparticle uptake, using the fluorescent dye inside the nanoparticles. Then, (E) the cells are sorted according to drug potency (activity/inactivity, I/0) using a viability stain, and activity is correlated to the internal drug or drug combination by measuring the DNA barcode concentration inside the cells. The fate of the untreated cells (e') is analyzed similarly, as a control.

FIG. 2. A schematic illustration of a non-limiting example of a high throughput approach for synthesizing and barcoding nanoparticles may employed. The microfluidic device (left). aqueous phase (bottom gray channels)—DNA and hydrophilic therapeutics are loaded into the particles. Aqueous pulsating flow is used to regulate shear rates in the microfluidic device. Organic phase (top white channels)—various lipid building blocks and hydrophobic drugs are combined using control pumps to alter the structural parameters of the particles. Each particle contains only one drug that corresponds to the barcode.

or labeled using additional means. (F) Confocal microscopy of DNA barcoded nanoparticles inside a 4T1 breast cancer cell. The cellular membrane is stained red (depicted gray), the nucleus blue (is depicted by an arrow), and the particles are depicted as white spots.

Figure 4:
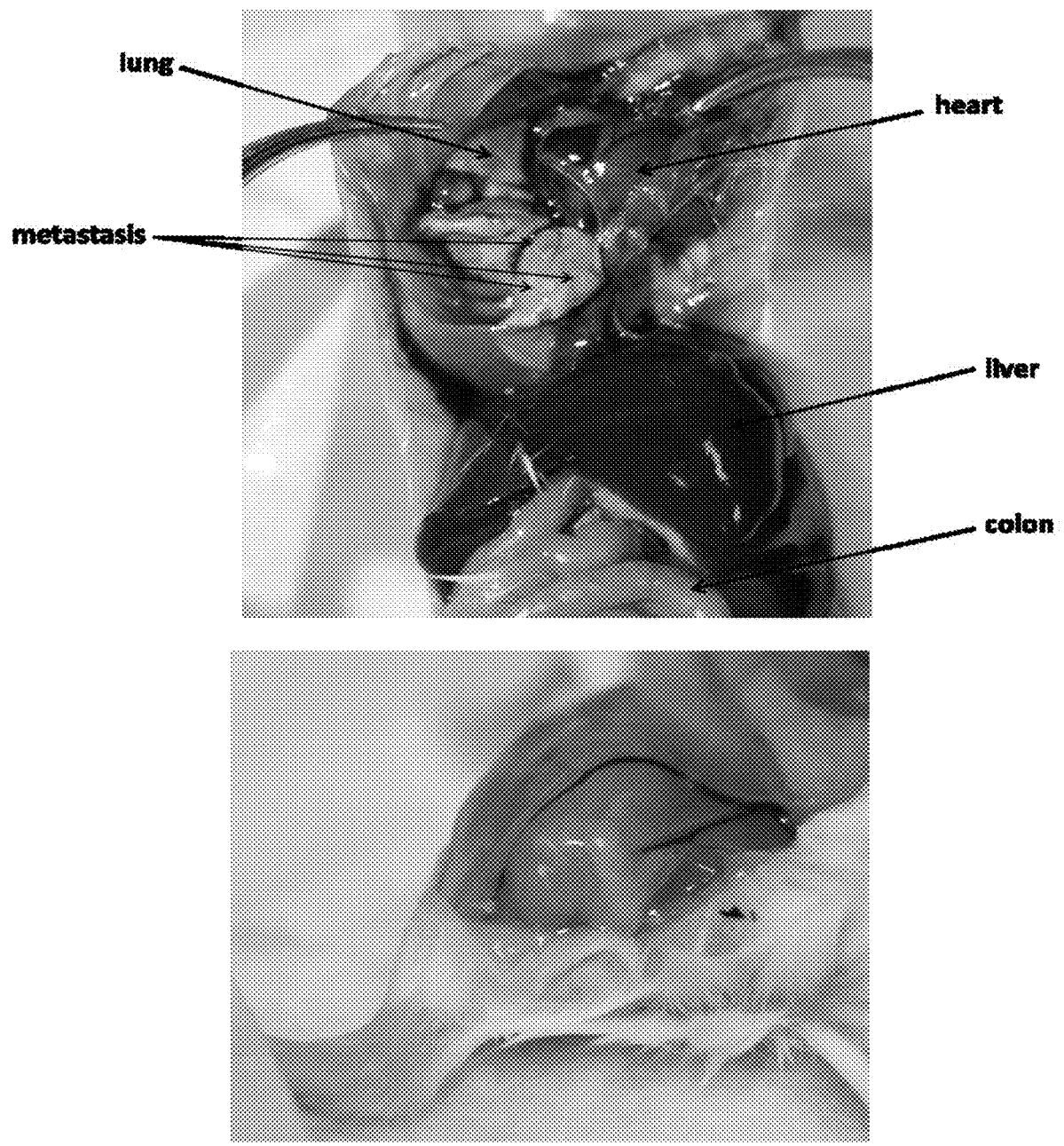

FIG. 4. A primary tumor and experimental metastasis. Triple-negative metastatic breast cancer models were established in BALB/c mice by local (primary tumor in the thigh, lower image) or intravenous (lung metastasis, upper image) injections of 4T1 cells. Animals bearing a primary tumor were injected with barcoded nanoparticles intravenously. The bio-distribution of the particles to the primary and metastatic sites was evaluated and the therapeutic potency of various drugs was screened.

Figure 5:
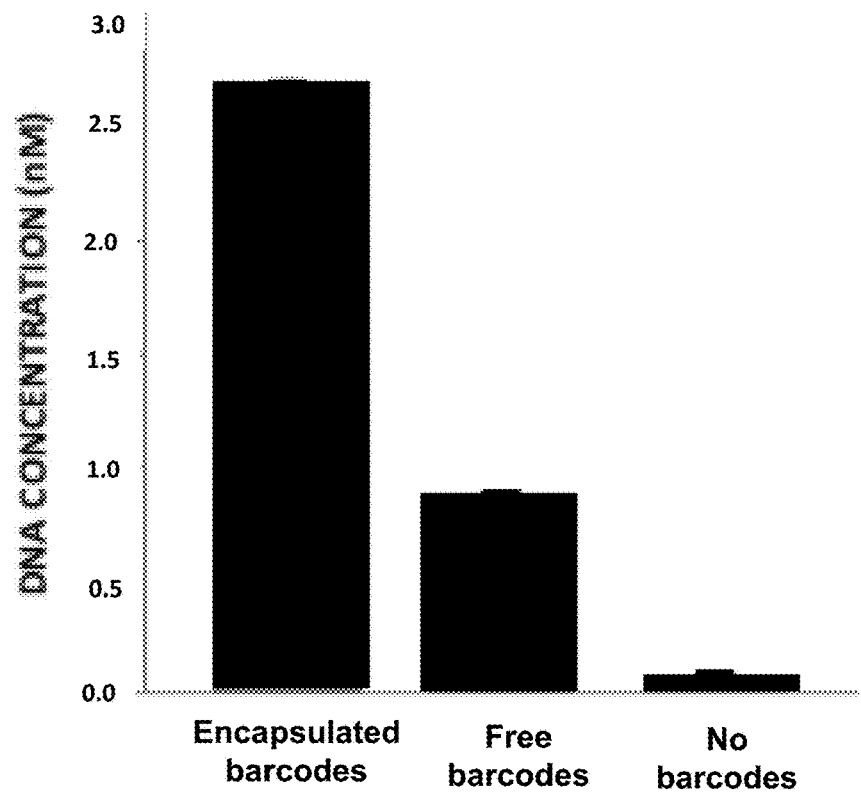

FIG. 5. A bar graph demonstrating barcode distribution inside a tumor tissue. The graph depicts barcode concentration between animals administered with free barcodes and animals administered with encapsulated barcodes. The control was free of barcodes.

Figure 6:
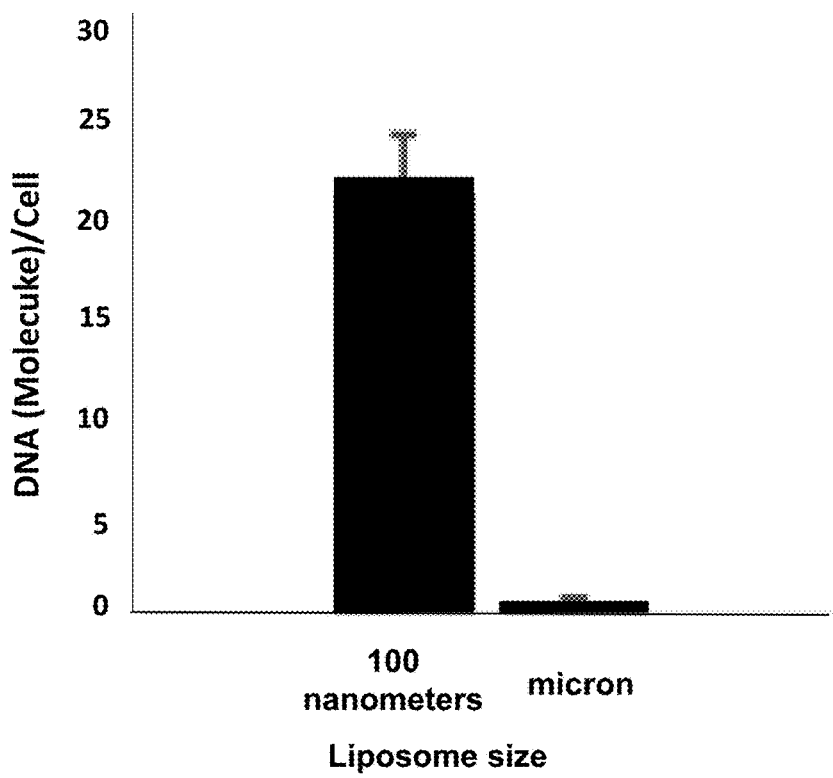

FIG. 6. A bar graph demonstrating DNA cell uptake of liposomes having different sizes.

Figure 7A:
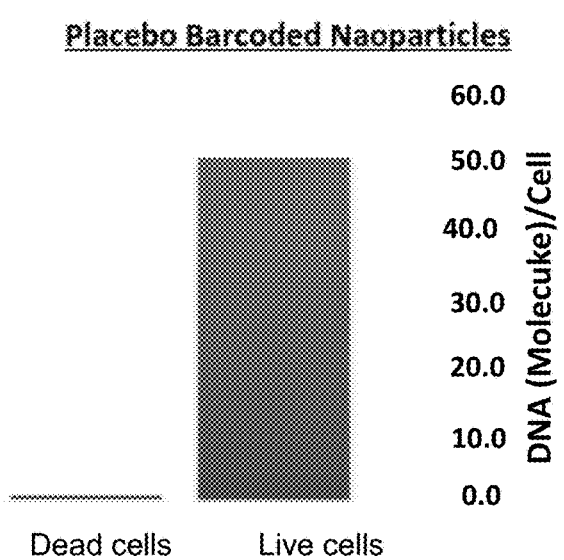
Figure 7B:
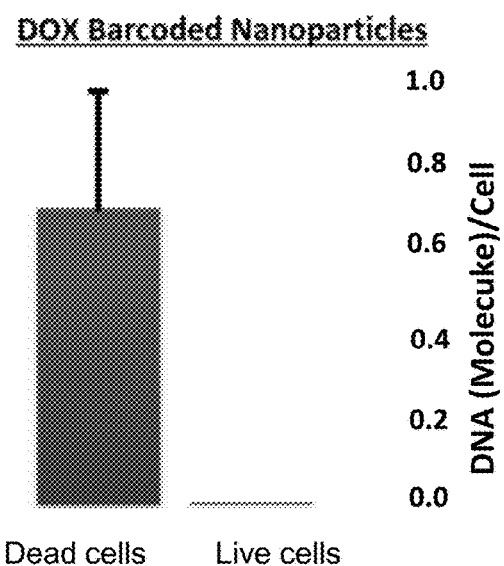
Figure 8A:
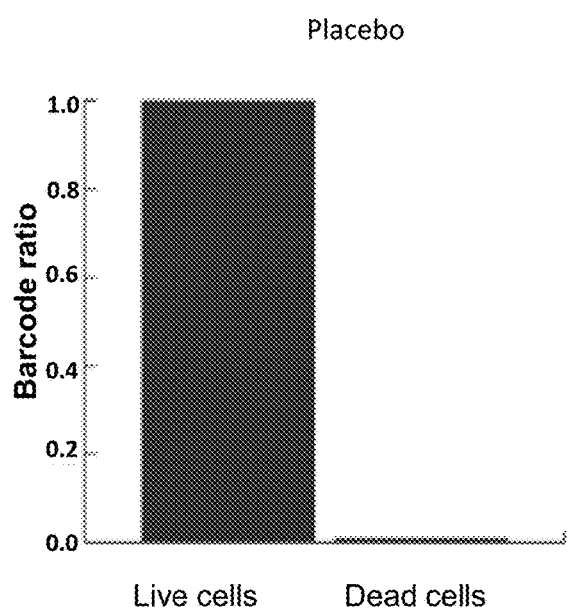
Figure 8B:
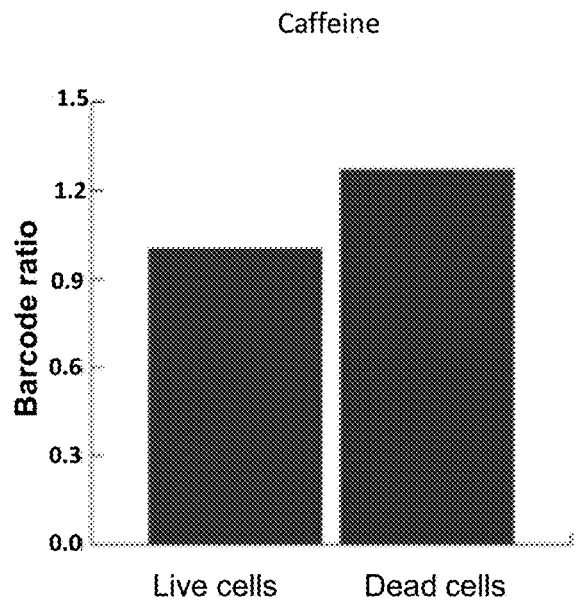
Figure 8C:
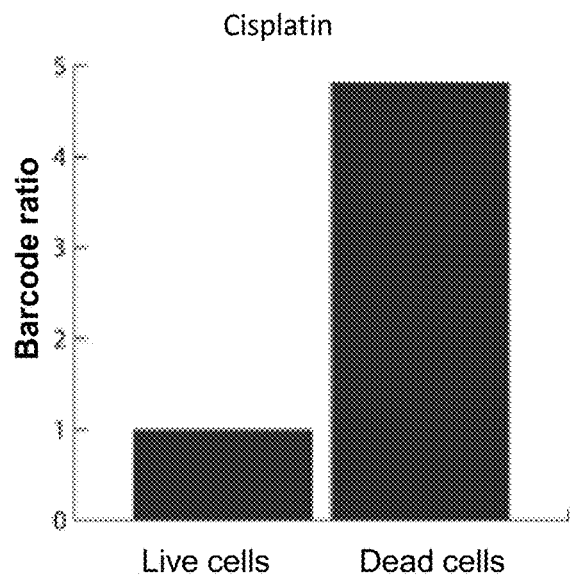
Figure 8D:
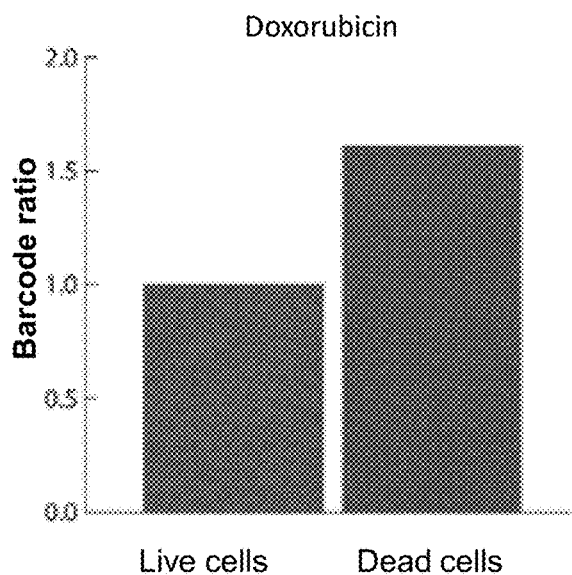
Figure 8E:
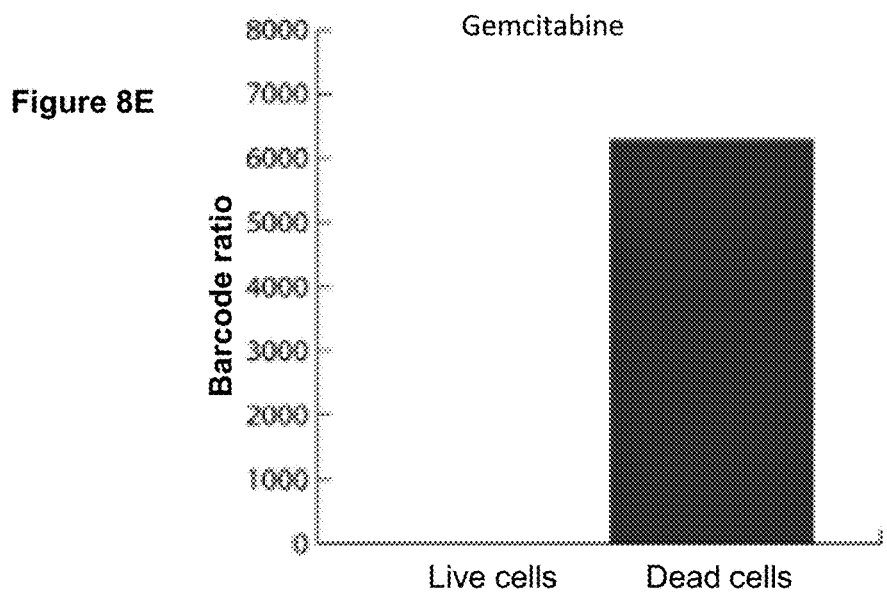
Figure 8F:
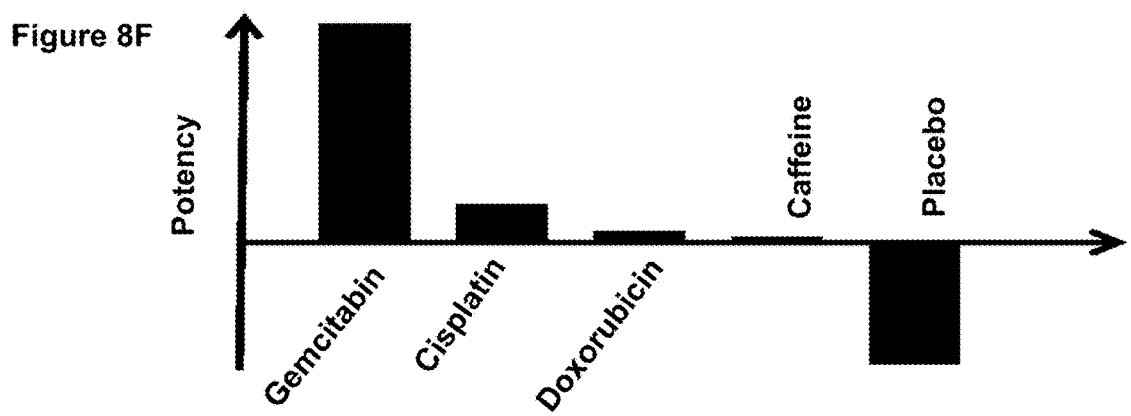

FIGS. 7A-B. A bar graph demonstrating barcode distribution inside the live and dead tumor cells following DOX treatment. Comparison of barcode distribution inside the tumor cells between placebo NPs (A) and barcoded NPs that contained DOX (B).

FIGS. 8A-F. A bar graph demonstrating theranostic barcoded nanoparticles. Barcoded nanoparticles containing control compounds or different drugs: placebo (A), caffeine (B), Cisplatin (C), Doxorubicin (D) and Gemcitabine (E), were injected simultaneously intravenously to BALB/c mice bearing a primary tumor in the hind thigh. 48 hours later, enabling the particle to accumulate in the tumor and perform the therapeutic activity, a biopsy was taken from the tumor. The biopsy tissue was then dissociated into a single-cell suspension, and the cells were screened according to their viability (live/dead). Elevated levels of the drug (gemcitabine, cisplatin) barcodes were found in the dead cells in comparison to the live cells. The neutral compound, caffeine, had similar barcode levels in both live and dead cells. y-axis indicates the number of barcodes found inside the cells. (F) The potency of the drugs was calculated by dividing the number of barcodes extracted from dead cells by the number of barcodes extracted from live cells for each drug. The values are presented in logarithmic scale.

Figure 9A:
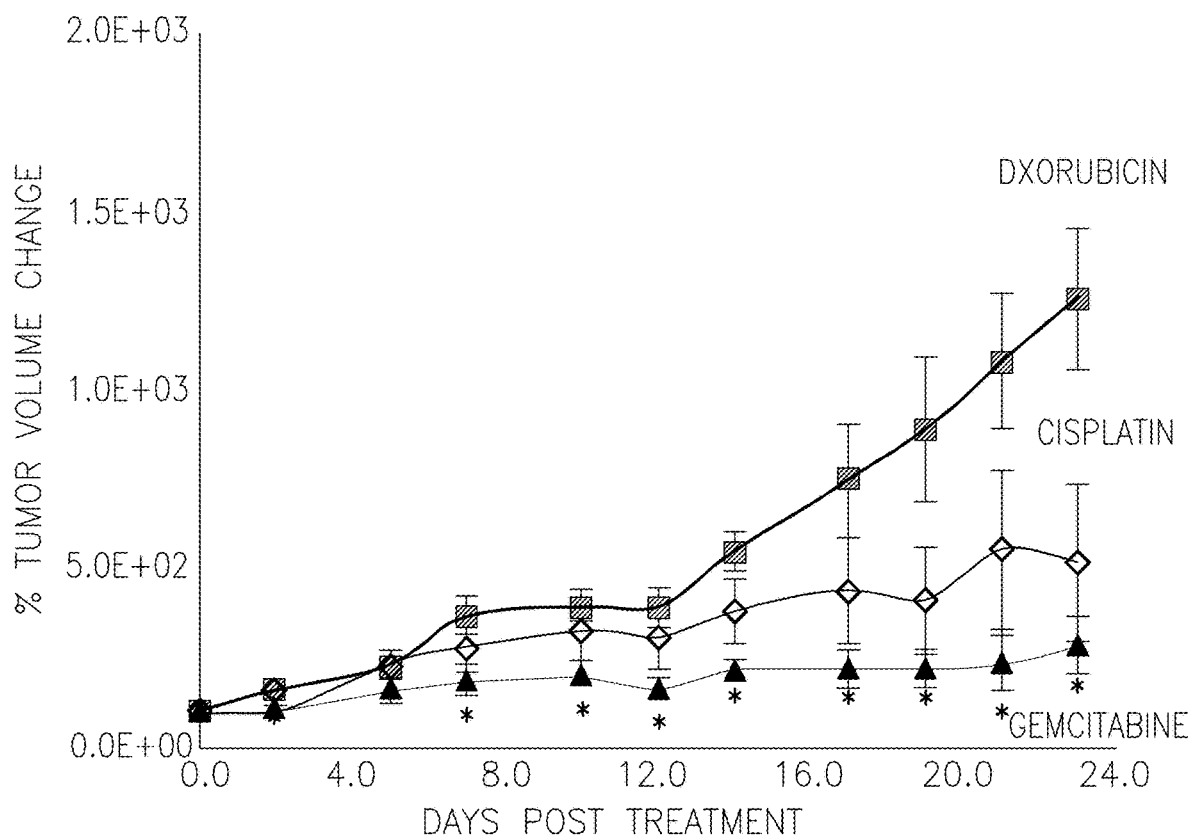
Figure 9B:
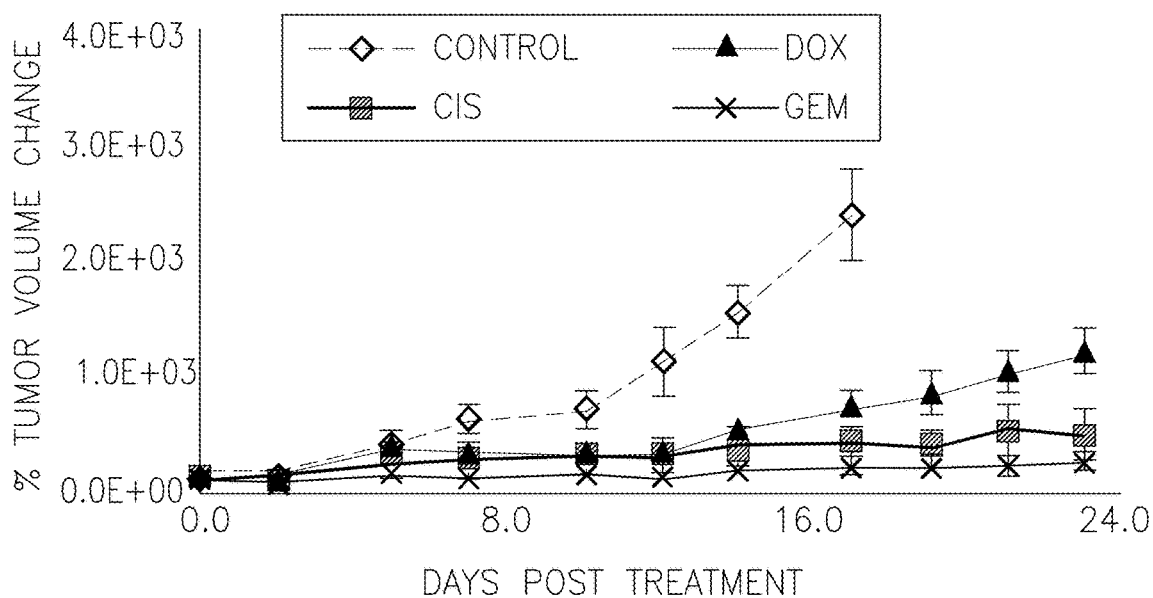

FIG. 9A-D. Therapeutic efficacy based on barcoding analysis. FIGS. 9A-B and D are bar graphs comparing tumor volume change between different therapeutic groups. Each group got a weekly dose of chemo drug Doxorubicin, Cisplatin, or Gemcitabine. The control group got saline. Representative tumor dimensions of each group. The tumor was extracted 23 days after starting the treatment. Tumor/Body weight of each group. Both tumor and body were measured at the day of the sacrifice (9C) The data was calculated as the mean+/−SDE of (n=6/group); *P<0.01; **** P<0.0001.

DETAILED DESCRIPTION OF THE INVENTION

The present invention provides compositions and methods useful for predicting and determining the therapeutic potency of a therapeutic agent or combinations of therapeutic agents against lesions. The compositions and methods disclosed herein enable tailoring treatments to address each patient's unique disease presentation.

As demonstrated herein below, carriers (e.g., nanoparticles) act as theranostic gauges for examining the therapeutic potency of a drug or drug combination inside a lesion (e.g., cancerous lesions), prior to beginning a treatment cycle.

In some embodiments, the carriers comprise a therapeutic agent and a corresponding barcode, and optionally a tag. Each carrier contains an extremely low dose of a drug, sufficient to treat only one cell, and far below the whole-body therapeutic threshold.

In some embodiments, there is provided a composition comprising at least one carrier, said at least one carrier comprises: a therapeutically effective amount of at least one therapeutic agent; a nucleic acid molecule uniquely identifying the at least one therapeutic agent; and optionally a tag (i.e., a tracer).

In some embodiments, the at least one therapeutic agent and the nucleic acid molecule, are encapsulated within the at least one carrier. In embodiments wherein the carrier further comprises a tag, the at least one therapeutic agent, the nucleic acid molecule, and the tag are encapsulated within the at least one carrier.

In another embodiment, there is provided a composition comprising a plurality of carriers, each carrier independently comprises at least one therapeutic agent and a nucleic acid molecule uniquely identifying said at least one therapeutic agent. In some embodiments, the composition comprises 1-5 types of carriers independently comprising a therapeutic agent or combination thereof. In some embodiments, the composition comprises 1-10 types of carriers independently comprising a therapeutic agent or combination thereof. In some embodiments, the composition comprises 1-200 carriers independently comprising a therapeutic agent or combination thereof. In some embodiments, the composition comprises 1-2000 carriers independently comprising a therapeutic agent or combination thereof. In some embodiments, the composition comprises 2-500 types of carriers independently comprising a therapeutic agent or combination thereof. As such, the compositions and methods of the invention provide simultaneous screening of multiple therapeutic agents or combination thereof at a single cell resolution. In some embodiments, the compositions and methods of the invention provide simultaneous screening of onco-therapeutic agents or combinations thereof at a single cell resolution.

As used herein "types of carriers" refers to carriers comprising an identical constitute of one or more therapeutic agent at a subsequently similar dose.

Therapeutic Agents

In some embodiments, said therapeutically effective amount is a substantially single-cell therapeutically effective amount.

As used herein, a "therapeutically effective amount" or "an amount effective" refers to an amount effective, at dosages and for periods of time necessary, to achieve the desired therapeutic result. The therapeutically effective amount of the therapeutic agent will depend on the nature of the disorder or condition and on the particular agent and can be determined by standard clinical techniques known to a person skilled in the art.

As used herein, a "single-cell therapeutically effective amount" refers to an effective amount sufficient to achieve the desired therapeutic result in a single cell. In particular embodiments, said single-cell therapeutically effective amount of a therapeutic agent is a considerably low dose of the agent compared to the minimum effective dose (MED) of said therapeutic agent. In some embodiments, said single-cell therapeutically effective amount is at most 0.1%, 0.01%, 0.001% or 0.0001% of the agent compared to the minimum effective dose (MED) of said therapeutic agent. In some embodiments, a "single-cell therapeutically effective amount" refers to the minimal effective amount sufficient to achieve the desired therapeutic result in a single cell. The amount may differ depending on cell type, drug type and/or duration of treatment.

In another embodiment, wherein the desired drug may react with other components of the composition, in order to provide a therapeutically effective amount of the drug per a single cell, an excess amount of the drug is used. For a non-limiting example, Cisplatin may react with the barcode DNA, therefore in order to provide a cell with a therapeutically effective amount of cisplatin an excess amount is encapsulated.

In some embodiments, a limited amount of a therapeutic agent may be used. As a non-limiting example, a single copy of Pseudomonas toxin is sufficient to kill a targeted cell.

In another embodiment, said single-cell therapeutically effective amount is substantially sufficient for modulating the state of a single cell or achieving the desired therapeutic result in a single cell. In another embodiment, said therapeutically effective amount is not more than 50%, 40%, 30, 20% or 10% of the amount sufficient for modulating the state of a single cell or achieving the desired therapeutic result in a single cell.

A therapeutic result may be, e.g., lessening of symptoms, prolonged survival, improved mobility, and the like. A therapeutic result need not be a "cure." A therapeutic result may also be prophylactic.

In another embodiment, said modulating the state of a single cell is selected from: modulating cell proliferation, modulating cell death, modulating cell drug resistance modulating cell function, activity or physiology. In some embodiments, modulating cell function or activity includes but is not limited to RNA transcription, translation of one or more proteins, including, for example, intra-cellular or trans-membrane proteins or lipids. In another embodiment, said modulating the state of a single cell includes the modulating the presence, absence, levels (e.g., increase or decrease), activation or inhibition of a cell component or biomarker. A cell component or biomarker includes but is not limited to a gene, a gene product (e.g., RNA, mRNA, miRNA) and an amino acid molecule (e.g., a protein). In some embodiments, cell activity is metabolic activity.

In some embodiments, said at least one therapeutic agent cannot cross the membrane of said cell. In said embodiments, said therapeutically effective amount may be at higher concentration, e.g., compared to concentration for treating a single cell. Examples of therapeutic agents which cannot cross the cell membrane include but are not limited to RNA and hydrophilic drugs.

Barcodes

In one embodiment, said barcode is one or more nucleic acid molecule. Nucleic acid molecules, such as DNA strands, present an unlimited number of barcoding options. As used throughout the invention "barcode", "DNA barcode", are all interchangeable with each other and have the same meaning. The nucleic acid molecule of the invention serving as a DNA barcode is a polymer of deoxynucleic acids or ribonucleic acids or both, and may be single-stranded or double-stranded, optionally containing synthetic, non-natural or altered nucleotide bases. In some embodiments, the nucleic acid molecule is labeled, for instance, with biotin, a radiolabel, or a fluorescent label.

As will be appreciated by a person skilled in the art, incorporation of unique DNA barcodes into the therapeutic agent carriers (encapsulation) allows the identification of individual therapeutic agents using assays including but not limited to microarray systems, PCR, nucleic acid hybridization (including "blotting") or high throughput sequencing.

In some embodiments, penetration of negatively charged DNA barcode through the negatively charged lipid bilayer of a cell is enabled by encapsulation of DNA barcode within the carrier of the invention.

In some embodiments, the sequence of the nucleic acid molecule is exclusive of sequences, patterns, signatures or any other nucleic acid sequences associated with a material/substance/particle that is naturally occurring in the environment or particularly naturally occurring in said cell being targeted by the method and composition of the invention. In additional embodiments, the sequence of the nucleic acid molecule is devoid of nucleotide sequences of more than 10 bases which can associate with a naturally occurring nucleotide sequence, and particularly of an exon. In another embodiment, said nucleic acid molecule comprises a sequence which is not substantially identical or complementary to said cell's genomic material (such as to prevent hybridization of the nucleic acid molecule with the cell's genomic material, particularly of said cell's exon and/or prevent false positive amplification results).

In some embodiments, said nucleic acid sequence may further serve as a molecular beacon. Said nucleic acid sequence may typically be a single strand molecule such as a hairpin shape. Said nucleic acid molecule may be used for detecting a complementary gene in the cell, such as for the detection of a genetic mutation inside the cell. In some embodiments, said nucleic acid has a sequence complementary to a mutation bearing sequence.

In some embodiments, said nucleic acid molecule comprises or consists of a pre-defined unique sequence. As used herein, the term "unique sequence" or "uniquely identifying" refers to a sequence based on an injective function (also termed one-to-one function) that preserves distinctness.

A unique barcode (e.g., a nucleic acid having a unique sequence) is suitable for identifying the corresponding at least one therapeutic agent within the carrier after implementing the prediction methods of the invention. Methods for the detection of the presence and identification of a nucleic acid sequence are known to a skilled artisan and include sequencing and array (e.g., microarray) systems capable of enhancing the presence of multiple barcodes (e.g., commercially available by Ilumina Inc.).

In some embodiments, such as where increased accuracy is desirable, the nucleic acid molecule has a length suitable for sequencing and/or amplification assays (e.g. PCR). In another embodiment, said nucleic acid molecule has a length suitable for loading into the carriers of the invention, preferably in the nanoscale. It should be appreciated that the length of said nucleic acid molecule is dependent on the type and size of the carrier used in the compositions and methods of the invention (e.g., shorter sequences are suitable for use in nanoparticles whereas longer sequences may be used in microparticles).

In another embodiment, said nucleic acid molecule has a length of at most 1000, at most 900, at most 800, at most 700, at most 600, at most 500, at most 450, at most 400, at most 350, at most 300, at most 250, at most 200, at most 190, at most 180, at most 170, at most 160, at most 150, at most 140, at most 130 or at most 120 bases, wherein each possibility represents a separate embodiment of the present invention. In another embodiment, said nucleic acid molecule has a length of at least 5, at least 6, at least 7, at least 8, at least 9, at least 10, at least 11, at least 12, at least 13, at least 14, at least 15, at least 16, at least 17, at least 18, at least 19 or at least 20 bases, at least 21, at least 22, at least 23, at least 24, at least 25, at least 26, at least 27, at least 28, at least 29 or at least 30 bases, at least 40, at least 50, at least 60, at least 70, at least 80, at least 90, at least 100 or at least 200, at least 300, at least 400 or at least 500 bases, wherein each possibility represents a separate embodiment of the present invention.

Non limiting examples of nucleic acid length include but is not limited to 5-50 bases, 5-40 bases, 5-30 bases, 5-25 bases, 5-24 bases, 5-23 bases, 5-22 bases, 5-21 bases, 5-20 bases, 5-19 bases, 5-18 bases, 5-17 bases, 5-16 bases or 5-15 bases, 15-50 bases, 15-60 bases, 15-70 bases, 15-80 bases, 15-90 bases, 15-100 bases, 15-200 bases, 15-250 bases or 15-500 bases.

In another embodiment, said nucleic acid molecule within each carrier has a concentration of one or more strands per carrier or per targeted cell. Determining the amount of the nucleic acid molecule is well under the capability of a person skilled in the art. In another embodiment, said one or more nucleic acid molecules is 1-10000 nucleic acid molecules. In another embodiment, said one or more nucleic acid molecules is 1-1000 nucleic acid molecules. In another embodiment, said one or more nucleic acid molecules is 1-5000 nucleic acid molecules. In another embodiment, said one or more nucleic acid molecules is 1-500 nucleic acid molecules. In another embodiment, said one or more nucleic acid molecules is 5-500 nucleic acid molecules. One skilled in the art will appreciate that the quantity of nucleic acid molecules in each particle may be pre-determined so as to suit the specific assay performed, e.g., sequencing and/or amplification assays.

According to some embodiments, each particle comprises a unique barcode. One skilled in the art will appreciate that bar-coding each particle (i.e., carrier) with a unique barcode may indicate the amount of particles that entered a single cell. In some embodiments, the invention provides a method of determining a therapeutic dose for treating a disease, the method comprises administering to a subject a composition comprising plurality of types carries, wherein each type carrier comprises one or more therapeutic agents, wherein each type of carrier differs in the dose of said one or more therapeutic agents.

According to some embodiments, each type of particle (i.e., carrier) comprises a unique barcode (e.g., nucleic acid sequence) identifying said type of carrier. According to some embodiments, each particle (i.e., carrier) comprises a unique barcode (e.g., nucleic acid sequence) identifying said type of carrier.

In another embodiment, said barcode is selected from the group consisting of: a rare earth element, a fluorophore, a chromophore, a chemilluminescent molecule, a magnetic particle, a dye, and a radioactive isotope.

In another embodiment, said barcode is a rare earth element. In another embodiment, said rare earth element is a lanthanide. In some embodiments, said lanthanide is selected from lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), Scandium (Sc) and yttrium (Y). In another embodiment, said rare earth element is a lanthanide. In some embodiments, said lanthanide is selected from La, Ce, Pr, Nd, Pm, Sm, Eu, Gd, Tb, Dy, Ho, Er, Tm, Yb and Lu.

The rare earth elements (e.g., lanthanides) may be useful when complexed with a luminescence label, and are generally utilized by combining a lanthanide complex with the sample of interest under conditions selected to yield a detectable optical response. The sample may be illuminated at a wavelength selected to elicit an optical response.

In another embodiment, said carrier within the composition further comprises additional agents (e.g. chemical or biological agent) for operably using said nucleic acid molecule as a barcode in a cell. Non-limiting examples of said agents include DNase or RNase, such as to prevent degradation by endogenous or exogenous enzymes of the DNA or RNA barcode, respectively.

In some embodiments, the barcode concentration in the solution forming the composition of the invention can vary between 2 to 100 micromols/liter ($\mu$M). In some embodiments, the barcode concentration in the solution can vary between 10 to 90 micromols/liter ($\mu$M). In some embodiments, the barcode concentration in the solution can vary between 20 to 80 micromols/liter ($\mu$M). In some embodiments, the barcode concentration in the solution can vary between 30 to 70 micromols/liter ($\mu$M).

In one embodiment, the composition described herein comprises a small number of nanoparticles, relative to the quantity of analyzed cells, so as to ensure a statistical significance of the data. Typically, when analyzing therapeutic effects of drug(s) on a tumor, average number of tumor cells in 1 millimeter$^3$ of cancer tissue is $10^6$ cells. The total number of cells in the whole tissue is several dozens of millions cells. Namely, the theoretical number of combination possibilities per cell is N! (factorial), where N is the number of barcodes, assuming that there are enough barcodes to enter each of the cells. To reduce the number of options, the number of barcoded nanoparticles per cell of analyzed tissue, is preferably less than 5.

In one embodiment, 1-5 types of carriers (i.e., barcoded nanoparticles) are present per cell. In another embodiment, the presence of 1-5 types of carriers per cell provides sufficient data and high signal to noise ratio (SNR). In another embodiment, cells comprising 1-5 types of carries per cell are analyzed. In another embodiment, cells comprising 1-4 types of carries per cell are analyzed.

The invention is based in part on the finding that the amount of particles that should be injected in order to achieve a presence of up to 5 barcode types per cell may be calculated by taking into account that 6-7% of an intravenously injected dose accumulates at the tumor site and 5% of the nanoparticles that actually reach the tumor site are taken up by cells, while the rest are trapped in the extracellular matrix (ECM).

In one embodiment, 1-200 particles per tumor cell are administered via intravenous injection. In another embodiment, 1-300 particles per tumor cell are administered via intravenous injection. In another embodiment, 1-400 particles per tumor cell are administered via intravenous injection. In another embodiment, 1-500 particles per tumor cell are administered via intravenous injection. In another embodiment, 1-1000 particles per tumor cell are administered via intravenous injection.

In another embodiment, 1-20 particles per tumor cell are administered intratumoraliy. In another embodiment, 1-10 particles per tumor cell are administered intratumorally. In another embodiment, 1-50 particles per tumor cell are administered intratumorally. In another embodiment, 1-100 particles per tumor cell are administered intratumorally.

In some embodiments, the amount of barcode molecules inside the particle is at least 1, or alternatively at least 5, or alternatively at least 10, or alternatively at least 20, or alternatively at least 30, or alternatively at least 40, or alternatively at least 50, or alternatively at least 60, or alternatively at least 70, or alternatively at least 80, or alternatively at least 90, or alternatively at least 100, or alternatively at least 500, or alternatively at least 1000, or alternatively at least 5000, or alternatively at least 10000 barcode molecules/particle. In some embodiments, the amount of barcode molecules inside the particle is at most 5, or alternatively at most 10, or alternatively at most 20, or alternatively at most 30, or alternatively at most 40, or alternatively at most 50, or alternatively at most 60, or alternatively at most 70, or alternatively at most 80, or alternatively at most 90, or alternatively at most 100, or alternatively at most 500, or alternatively at most 1000, or alternatively at most 5000 barcode molecules/particle. In some embodiments, the amount of barcode molecules inside the particle ranges between 5-100 barcode molecules/particle. In some embodiments, the amount of barcode molecules inside the particle ranges between 10-90 barcode molecules/particle. In some embodiments, the amount of barcode molecules inside the particle ranges between 20-80 barcode molecules/particle. Each possibility represents a separate embodiment of the invention. In some embodiments, the amount of barcode molecules inside the particle ranges between 1-1000 barcode molecules/particle. In some embodiments, the amount of barcode molecules inside the particle ranges between 1-10000 barcode molecules/particle.

Tags

In another embodiment, the one or more carriers of the invention further comprise at least one tag or detectable moiety. In some embodiments, an identical tag is used for all carriers. In other embodiments, a unique tag is used for a sub-set of carriers.

Tags which may be used in the compositions and methods of the invention include but are not limited to a fluorophore, a chromophore, a chemilluminescent molecule, a radiomarker, a metal, a rare earth, magnetic particle or a dye.

In some embodiments, the tag or detectable moiety is a tag useful in assay including but not limited to immunological assay such as ELISA, bead-, chip- or plate-based multiplex immunoassays, mass spectrometry, electrophoresis, immunonephelometry, immunoturbidimetry, enzymatic assays, colorimetric or fluorometric assays e.g. evaluable by photometry, and fluorescence-associated cell sorting (FACS)-based analyses or by other clinically established assays. All these methods are well known to the person of skill in the art, and described in the literature.

Typically, the amount of the tag will depend on the assay to be performed and can be determined by and is well under the capability of a person skilled in the art. In some embodiments, the carrier comprises one molecule or more molecules of said tag.

Carriers

In some embodiments, there is provided carriers for therapeutic agent(s), nucleic acid sequences useful for DNA bar-coding said therapeutic agent(s) and optionally a tag. Said carrier used to practice the methods of the invention may target specific molecules, including biologic molecules, such as polypeptide, including cell surface polypeptides, e.g., polypeptides on abnormally growing cells, cancer cells, immune cells and degenerative cells.

In alternative embodiments, the invention provides carriers in the form of nanoparticles and liposomal membranes comprising (in addition to comprising compounds used to practice the methods of the invention) molecules, e.g., peptides or antibodies, that selectively target abnormally growing, diseased, infected, dysfunctional and/or cell receptors.

In some embodiments, said at least one carrier is in a form of a vesicle such as that carried materials (therapeutic agent, nucleic acid molecule and optionally a tag) are inside an internal core. In some embodiments, said at least one carrier is a lipid-based particle. In another embodiment, said lipid-based particle is a liposome. In another embodiment, said at least one carrier is a micelle.

In some embodiments, the solution is inert to and does not affect the designated cell. In some embodiments, all components of the composition, besides the therapeutic agent, are inert and do not affect the designated cell. In some embodiments, the solution is an aqueous solution. In another embodiment, the composition of the invention is devoid of a cationic surfactant (as it may affect a cell and/or affect the activity of the therapeutic agent, and prevent accurate analysis of the effect of the therapeutic agent).

In some embodiments, said at least one carrier is in a form of a vesicle such as that carried materials (therapeutic agent, nucleic acid molecule and optionally a tag) form a complex/particulate with the carried materials with or without the another agent such as a polymer/protein/salt. In some embodiments, said at least one carrier forms a dendrimer like structure in which the components are conjugated to the polymeric backbone or complexed via van der Waals or hydrophobic interactions.

In some embodiments, said at least one carrier is a polymeric nanoparticle. In some embodiments, said at least one carrier is a nanogel. In some embodiments, said at least one carrier is a metallic nanoparticle (e.g., a gold or iron oxide nanoparticle). In some embodiments, said at least one carrier is carbon nanotube. In some embodiments, said at least one carrier is a layer by layer particle. In some embodiments, said at least one carrier is a sol-gel ceramic particles. In some embodiments, said at least one carrier is a protein complex with the drug.

In some embodiments, said at least one carrier forms a dendrimer like structure in which the components are conjugated to the polymeric backbone or complexed via van der Waals or hydrophobic interactions.

In one embodiment, the carrier (e.g., liposome) is less than 500 nm in diameter to facilitate its entrance through the extracellular matrix to a cell. In one embodiment, the carrier (e.g., liposome) is less than 400 nm in diameter to facilitate its entrance through the extracellular matrix to a cell.

In one embodiment, the carrier (e.g., liposome) is less than 300 nm in diameter, less than 250 nm, less than 200 nm in diameter, less than 150 nm in diameter, less than 100 nm in diameter, less than 50 nm in diameter, less than 20 nm in diameter, less than 10 nm in diameter or less than 5 nm in diameter. In another embodiment, the carrier (e.g., liposome) is at least 1 nm in diameter, at least 5 nm in diameter, at least 10 nm in diameter, at least 20 nm in diameter, at least 30 nm in diameter, at least 40 nm in diameter, at least 50 nm in diameter, at least 60 nm in diameter, at least 70 nm in diameter, at least 80 nm in diameter, at least 90 nm in diameter, at least 100 nm in diameter, at least 1500 nm in diameter, at least 200 nm in diameter, at least 250 nm in diameter or at least 300 nm in diameter. Each possibility represents a separate embodiment of the invention.

In another embodiment, the carrier is 1-300 nm in diameter. In another embodiment, the carrier is 10-250 nm in diameter. In another embodiment, the carrier is 5-250 nm in diameter. In another embodiment, the liposome is 20-150 nm in diameter. In another embodiment, the liposome is 5-150 nm in diameter. In another embodiment, the liposome is 20-150 nm in diameter.

In some embodiments, a carrier for intravenous administration is 5-250 nm in diameter. In some embodiments, wherein the carrier for intravenous administration is a liposome, the carrier is 40-250 nm in diameter. In some embodiments, a carrier for intratumoral administration is 5-300 nm in diameter. In some embodiments, wherein the carrier for intratumoral administration is a liposome, the carrier is 40-300 nm in diameter.

In some embodiments, the morphology of the carrier may be spherical or substantially spherical, non-spherical (e.g. elliptical, tubular, etc.), irregular etc.

The use of liposomal transfer vehicles to facilitate the delivery of therapeutic agents and nucleic acids to target cells is contemplated by the present invention. Liposomes (e.g., liposomal lipid nanoparticles) are generally useful in a variety of applications in research, industry, and medicine, particularly for their use as transfer vehicles of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, ibid.). Bilayer membranes of the liposomes can also be formed by amphiphilic polymers and surfactants (e.g., polymerosomes, niosomes, etc.).

In one embodiment, the carrier may be selected and/or prepared to optimize delivery of the therapeutic agent and nucleic acid molecule (the DNA barcode) to a target cell. For example, if the target cell is a hepatocyte the properties of the transfer vehicle (e.g., size, charge and/or pH) may be optimized to effectively deliver such transfer vehicle to the target cell. Alternatively, if the target cell is the central nervous system (e.g., for therapy predication of neurodegenerative diseases), selection and preparation of the transfer vehicle must consider penetration of, and retention within the blood brain barrier and/or the use of alternate means of directly delivering such transfer vehicle to such target cell.

The process of incorporation of a desired entity into a liposome is often referred to as "loading" (Lasic, et al., FEBS Lett., 312: 255-258, 1992). The liposome-incorporated therapeutic agents, nucleic acids and/or tag, may be completely or partially located in the interior space of the liposome, within the bilayer membrane of the liposome. Incorporation of an agent into liposomes is also referred to herein as "encapsulation" wherein the agent is entirely contained within the interior space of the liposome. Typically, for encapsulation of an agent within a carrier (e.g. liposome) a chemical linkage, such as a covalent linkage between the agent and the carrier, is not required. The purpose of incorporating an agent into a transfer vehicle, such as a liposome, is often to protect the agent from an environment which may contain enzymes or chemicals that degrade the agent (e.g., nucleic acids) and/or systems or receptors that cause the rapid excretion of the agent. Accordingly, in a preferred embodiment of the present invention, the selected transfer vehicle is capable of enhancing the stability of the therapeutic agent and the nucleic acid molecule and optionally the tag contained therein. The liposome can allow the encapsulated agents to reach the target cell and/or may preferentially allow the encapsulated agents to reach the target cell, or alternatively limit the delivery of the agents to other undesired target sites or cells.

In some embodiments the carrier facilitates penetration of the encapsulated therapeutically effective amount of at least one therapeutic agent, the nucleic acid molecule uniquely identifying the at least one therapeutic agent and the optional tag to a cell. In some embodiments, the penetration of therapeutically effective amount of at least one therapeutic agent, the nucleic acid molecule uniquely identifying the at least one therapeutic agent and the optional tag to a cell is enabled by encapsulation within a carrier.

In some embodiments, liposomal transfer vehicles are prepared to encapsulate one or more desired agent such that the compositions demonstrate a high transfection efficiency and enhanced stability. While liposomes can facilitate introduction of nucleic acids into target cells, the addition of polycations (e.g., poly L-lysine and protamine), as a copolymer can facilitate, and in some instances markedly enhance the transfection efficiency of several types of cationic liposomes by 2-28 fold in a number of cell lines both in vitro and in vivo. (See N. J. Caplen, et al., Gene Ther. 1995; 2: 603; S. Li, et al., Gene Ther. 1997; 4, 891).

In another embodiment, said at least one carrier is a nanoliposome or lipid nanoparticle. Nanoliposomes are able to enhance the performance of bioactive agents by improving their solubility and bioavailability, in vitro and in vivo stability, as well as preventing their unwanted interactions with other molecules. Another advantage of nanoliposomes is cell-specific targeting, which is a prerequisite to attain drug concentrations required for optimum therapeutic efficacy in the target cell while minimizing adverse effects on healthy cells and tissues.

As used herein, the phrase "lipid nanoparticle" refers to a transfer vehicle comprising one or more lipids (e.g., cationic lipids, non-cationic lipids, and PEG-modified lipids). Preferably, the lipid nanoparticles are formulated to deliver one or more agents to one or more target cells. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine. In one embodiment, the transfer vehicle is selected based upon its ability to facilitate the transfection of a nucleic acid to a target cell.

The invention contemplates the use of lipid nanoparticles as transfer vehicles comprising a cationic lipid to encapsulate and/or enhance the delivery of nucleic acid into the target cell. As used herein, the phrase "cationic lipid" refers to any of a number of lipid species that carry a net positive charge at a selected pH, such as physiological pH. The contemplated lipid nanoparticles may be prepared by including multi-component lipid mixtures of varying ratios employing one or more cationic lipids, non-cationic lipids and PEG-modified lipids. Several cationic lipids have been described in the literature, many of which are commercially available.

Suitable cationic lipids for use in the compositions and methods of the invention include those described in international patent publication WO 2010/053572, incorporated herein by reference. In certain embodiments, the compositions and methods of the invention employ a lipid nanoparticles comprising an ionizable cationic lipid. In some embodiments, the cationic lipid N-[1-(2,3-dioleyloxy)propyl]-N,N,N-trimethylammonium chloride or "DOTMA" is used. (U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis, cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl[1, 3]-dioxolane or "DLin-K-XTC2-DMA", and 2-(2,2-di((9Z, 12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28:172-176 (2010)), or mixtures thereof (Heyes, J., et al., J Controlled Release 107: 276-287 (2005); Morrissey, D V., et al., Nat. Biotechnol. 23(8): 1003-1007 (2005); PCT Publication WO2005/121814A1).

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000. (Invitrogen), FUGENE, TRANSFECTAM (DOGS), and EFFECTENE.

Also contemplated are cationic lipids such as the dialkylamino-based, imidazole-based, and guanidinium-based lipids. For example, certain embodiments are directed to a composition comprising one or more imidazole-based cationic lipids.

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipids together which comprise the transfer vehicle (e.g., a lipid nanoparticle). The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

The present invention also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the transfer vehicle.

In some embodiments, the transfer vehicle (e.g., a lipid nanoparticle) is prepared by combining multiple lipid and/or polymer components. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells and the characteristics of the agents to be delivered. Additional considerations include, for example, the saturation of the alkyl chain, as well as the size, charge, pH, pKa, fusogenicity and toxicity of the selected lipid(s).

The liposomal transfer vehicles for use in the compositions of the invention can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, the compositions of the invention may be loaded with diagnostic radionuclide, fluorescent materials or other materials that are detectable in both in vitro and in vivo applications.

In some embodiments, the nanoparticle carriers of the invention are fabricated of lipids using an in-line microfluidic setup adapted to accommodate high-throughput synthesis and labeling of the particles. Such fabrication methods are known in the art, e.g., Jahn et al., 2007, Langmuir 23, 6289-6293. Typically, particles of appropriate sizes to accommodate the therapeutic payload are fabricated.

Chemical agents may be loaded into stable HSPC particles, for examples as shown by Schroeder et al., 2007, Langmuir 23, 4019-4025. Biological therapeutics (protein/RNA) may be synthesized inside 'protein producing nanoparticles'. In some embodiments, a synthetic nanoparticle is controllably triggered to synthesize proteins and RNA at a target site, as shown in Schroeder, A. et al. Nano Lett 12, 2685-2689, (2012). These nanoparticles consist of lipid vesicles filled with the molecular machinery responsible for transcription and translation, including amino acids, ribosomes, and DNA caged with a photo-labile protecting group. The particles serve as nano-factories capable of producing RNA/proteins. In vitro and in vivo, protein/RNA synthesis may be spatially and temporally controllable, and can be initiated by illuminating micron-scale tissue regions on the timescale of milliseconds. As such, this platform may be used to screen RNA (Png et al. 2012 Nature 481, 190-194) and proteins for their activity, e.g., anti-cancer activity.

In some embodiments, the nanoparticle (e.g., carrier) of the invention is a nanoparticle wherein the liposome-forming lipid constitutes 40-100% mol of the nanoparticle. In some embodiments, the nanoparticle of the invention comprises 0-50% % mol cholesterol. In some embodiments, the nanoparticle of the invention comprises 1-8% mol PEG-lipid. In some embodiments, the nanoparticle of the invention comprises 0-10% mol of a functional lipid (e.g., a cationic lipid or a lipid with a targeting moiety).

As used herein and in the art, mol percent ("% mol") refers to a percent of a particular component or compound based on the total mols of the components or compounds constituting the nanoparticle. For example, if a nanoparticle contains three mols of compound A and one mol of compound B, then the compound A comprises 75 mol % of the mixture and the compound B comprises 25 mol %.

In some embodiments, the nanoparticle (e.g., carrier) of the invention comprises 40-70% mol liposome-forming lipid. In some embodiments, the nanoparticle of the invention comprises 20-50% % mol cholesterol. In some embodiments, the nanoparticle of the invention comprises 4-8% mol PEG-lipid. In some embodiments, the nanoparticle of the invention comprises 0-3% mol of a functional lipid (e.g., a cationic lipid or a lipid with a targeting moiety). According to specific embodiment, a nanoparticle comprising 40-70% mol liposome-forming lipid, 20-50% % mol cholesterol, 4-8% mol PEG-lipid and 0-3% mol of a functional lipid is suitable for intravenous administration.

In some embodiments, the nanoparticle (e.g., carrier) of the invention comprises 50-80% mol liposome-forming lipid. In some embodiments, the nanoparticle of the invention comprises 0-50% % mol cholesterol. In some embodiments, the nanoparticle of the invention comprises 0-3% mol PEG-lipid. In some embodiments, the nanoparticle of the invention comprises 4-8% mol of a functional lipid (e.g., a cationic lipid or a lipid with a targeting moiety). According to specific embodiment, a nanoparticle comprising 50-80% mol liposome-forming lipid, 0-50% % mol cholesterol, 0-3% mol PEG-lipid and 4-8% mol of a functional lipid is suitable for intratumoral administration.

Theranostic Use

According to some embodiments, there is provided a composition comprising a plurality of carriers independently comprising a therapeutically effective amount of at least one therapeutic agent and a nucleic acid molecule uniquely identifying said at least one therapeutic agent, for use in predicting the response of a subject afflicted with a disease to a therapeutic agent.

According to some embodiments, there is provided a method for predicting the response of a subject afflicted with a disease to a therapeutic agent, the method comprising the steps of:
  (a) administering to the subject a composition comprising a plurality of carriers independently comprising a therapeutically effective amount of at least one therapeutic agent and a nucleic acid molecule uniquely identifying said at least one therapeutic agent; and
  (b) identifying, in a sample obtained from said subject, the efficacy of said at least one therapeutic agent by the unique nucleic acid molecule;
Thereby predicting the response of a subject afflicted with a disease to a therapeutic agent.

In another embodiment, said method further comprises a step of sequencing said nucleic acid molecule. In another embodiment, said method further comprises a step of amplifying said nucleic acid molecule. Methods for amplifying and sequencing nucleic acids are well known to a person skilled in the art.

In another embodiment, said method further comprises a washing and DNAse treatment step, following incubation of the agents with the target cells. In another embodiment, said sample is disassembled into a single-cell suspension prior to determining therapeutic efficacy. Methods for disassembling cell samples into single-cell suspensions are known in the art and may include for instance gentleMACS™ Dissociators.

In another embodiment, said method further comprising a cell sorting step. Methods of cell sorting are well known in the art and include but are not limited to FACS, magnetic bead sorting, ELISA, microfluidic based sorting, cell-tension based sorting and the like. According to advantageous embodiments, the activity of each therapeutic agent is analyzed by sorting the target cells and correlating the cell status (e.g. live/dead cells) to the DNA barcode. In additional embodiments, this approach enables screening multiple drugs for their patient-specific and cell-specific activity.

In embodiments, the method disclosed herein includes providing sustained amounts of time for the therapeutic agent to execute its therapeutic activity. The sustained amounts of time before sampling the targeted cells will depend on the nature of the disorder or condition and on the particular agent and can be determined by standard clinical techniques known to a person skilled in the art. As non-limiting examples, sustained amounts of time include about 24, about 30, about 48 hours, or more 24 hours after administration of the composition. Each possibility represents a separate embodiment of the invention. In some embodiments, in order to avoid DNases degradation of the barcode inside the cells the sustained amounts of time is less than 72 hours.

In some embodiments, the sustained amounts of time before sampling the targeted cells range from 24 to 72 hours. In some embodiments, the sustained amounts of time before sampling the targeted cells range from 24 to 48 hours. In other embodiments, the sustained amounts of time before sampling the targeted cells range from 30-48 hours. In other embodiments, the sample is obtained at least 24 hours following administration of the composition. In other embodiments, the sample is obtained at least 30 hours following administration of the composition. In other embodiments, the sample is obtained at least 48 hours following administration of the composition. In other embodiments, the sample is obtained at most 48 hours following administration of the composition. In other embodiments, the sample is obtained at most 60 hours following administration of the composition. In other embodiments, the sample is obtained at most 72 hours following administration of the composition. In other embodiments, the sample is obtained between 24-48 hours following administration of the composition. In other embodiments, the sample is obtained between 30-48 hours following administration of the composition. The exact time frame for sampling the targeted cells may be determined according several factors, including the type and amount of barcode used and the therapeutic agent being examined. As a non-limiting example, nucleic acid molecules are typically susceptible to degradation 48 hours following administration (particularly systemic administration) whereas rare earth elements can be detected for longer periods of time. In other embodiments, therapeutic agents differ by the time they act on a target cell.

In some embodiments, the therapeutic agent (e.g., cisplatin) comprises a unique barcode. One skilled in the art will appreciate that in such embodiments, said carrier may comprise the therapeutic agent (e.g., cisplatin) and there is no need to add an additional barcode.

In another embodiment, said composition is formulated for systemic administration. In another embodiment, said systemic administration is intravenous injection. In another embodiment, said administration is injection into tissue such as intratumoral injection.

In some aspects, there is provided a composition comprising at least one cell comprising 1-4 types of carriers of the invention. In some embodiments, there is provided a composition comprising at least one cell comprising 1-4 types of carriers, each type of carrier independently to comprises a single cell therapeutically effective amount of at least one therapeutic agent; and 1-10,000 nucleic acid molecules uniquely identifying the at least one therapeutic agent. In some embodiments, there is provided a composition comprising a plurality of cells, each cell comprising 1-4 types of carriers, and each type of carrier independently comprises a single cell therapeutically effective amount of at least one therapeutic agent; and 1-10,000 nucleic acid molecules uniquely identifying the at least one therapeutic agent.

The methods and compositions of the present invention may be used to preferentially target a vast number of target cells. For example, contemplated target cells include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardio myocytes, skeletal muscle cells, beta cells, pituitary cells, synovial lining cells, ovarian cells, testicular cells, fibroblasts, B cells, T cells, reticulocytes, leukocytes, granulocytes and tumor cells. As used herein, "tumor cells" include primary cancer cells as well as metastatic cells.

As used herein, the term "subject" refers to any animal (e.g., a mammal), including, but not limited to, humans, non-human primates, rodents, and the like, to which the compositions and methods of the present invention are administered. In some embodiments, the terms "subject" and "patient" are used interchangeably herein in reference to a human subject. In other embodiments, the terms "subject" and "patient" are used interchangeably herein in reference to a non-human subject.

In some embodiments, the method of the invention is useful for determining or predicting the response of a subject afflicted with a malignant disease to a therapeutic agent. In some embodiments, said malignant disease is cancer, cancer metastasis and pre-malignant lesions.

Examples of cancer therapeutic agents include, e.g., but are not limited to Abiraterone, Acitretin, Aldesleukin, Alemtuzumab, Amifostine, Amsacrine, Anagrelide, Anastrozole, Arsenic, Asparaginase, Asparaginase Erwinia, Axitinib, azaCITItidine, BCG, Bendamustine, Bevacizumab, Bexarotene, Bicalutamide, Bleomycin, Bortezomib, Brentuximab, Bromocriptine, Buserelin, Busulfan, Cabazitaxel, Cabergoline, Capecitabine, CARBOplatin, Carmustine, Cetuximab, Chlorambucil, CISplatin, Cladribine, Clodronate, Crizotinib, Cyclophosphamide, CycloSPORINE, Cytarabine, Dacarbazine, Dactinomycin, Dasatinib, DAUNOrubicin, Degarelix, Denosumab, Dexamethasone, Dexrazoxane, DOCEtaxel, DOXOrubicin, DOXOrubicin pegylated liposomal, Enzalutamide, Epirubicin, Eribulin, Erlotinib, Estramustine, Etoposide, Everolimus, Exemestane, Filgrastim, Fludarabine, Fluorouracil, Flutamide, Fulvestrant, Gefitinib, Gemcitabine, Goserelin, Hydroxyurea, IDArubicin, Ifosfamide, Imatinib, Iniparib, Interferon alfa-2b, Ipilimumab, Irinotecan, Ixabepilone, Lambrolizumab, Lanreotide, Lapatinib, Lenalidomide, Letrozole, Leucovorin, Leuprolide, Lomustine, Mechlorethamine, medroxyPROGESTERone, Megestrol, Melphalan, Mercaptopurine, Mesna, Methotrexate, mitoMYCIN, Mitotane, mitoXANTRONE, Nilotinib, Nilutamide, Octreotide, Ofatumumab, Oxaliplatin, PACLitaxel, ACLitaxel nanoparticle, albuminbound (nab), Pamidronate, Panitumumab, Pazopanib Pemetrexed, Pertuzumab, Porfimer, Procarbazine, Quinagolide, Raltitrexed, Reovirus Serotype 3-Dearing Strain, riTUXimab, Romidepsin, Ruxolitinib, SORAfenib, Streptozocin, SUNItinib, Tamoxifen, Temozolomide, Temsirolimus, Teniposide, Testosterone, Thalidomide, Thioguanine, Thiotepa, Thyrotropin alfa, Tocilizumab, Topotecan, Trastuzumab (HERCEPTIN®), Trastuzumab, Emtansine (KADCYLA®), Treosulfan, Tretinoin, Vemurafenib, vinBLAstine, vinCRIstine and Vinorelbine.

Examples of chemotherapeutic agents used as a therapeutic agent include, e.g., but are not limited to, e.g., alkylating agents (e.g., cyclophosphamide, ifosfamide, melphalan, chlorambucil, aziridines, epoxides, alkyl sulfonates), cisplatin and its analogues (e.g., carboplatin, oxaliplatin), antimetabolitites (e.g., methotrexate, 5-fluorouracil, capecitabine, cytarabine, gemcitabine, fludarabine), toposiomerase interactive agents (e.g., camptothecin, irinotecan, topotecan, etoposide, teniposide, doxorubicin, daunorubicin), antimicrotubule agents (e.g., vinca alkaloids, such as vincristine, vinblastine, and vinorelbine; taxanes, such as paclitaxel and docetaxel), interferons, interleukin-2, histone deacetylase inhibitors, monoclonal antibodies, estrogen modulators (e.g., tamoxifen, toremifene, raloxifene), megestrol, aromatase inhibitors (e.g., letrozole, anastrozole, exemestane, octreotide), octreotide, anti-androgens (e.g., flutamide, casodex), kinase and tyrosine inhibitors (e.g., imatinib (STI571 or Gleevac); gefitinib (Iressa); and erlotinib (Tarceva), etc.

See, e.g. Cancer: Principles and Practice of Oncology, 7th Edition, Devita et al, Lippincott Williams & Wilkins, 2005, Chapters 15, 16, 17, and 63).

In some embodiments, the method of the invention is useful for determining or predicting the response of a subject afflicted with an inflammatory disease or disorder to a therapeutic agent.

In some embodiments, the method of the invention is useful for determining or predicting the response of a subject afflicted with a degenerative disease or disorder to a therapeutic agent. In one embodiment, said degenerative disease is osteoarthritis.

In some embodiments, the method of the invention is useful for determining or predicting the response of a subject afflicted with a neurological disease or disorder to a therapeutic agent.

As used herein, the term "about" when combined with a value refers to plus and minus 10% of the reference value. For example, a length of about 1000 nanometers (nm) refers to a length of 1000 nm+−100 nm.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Liposome Synthesis/Preparation

Liposomes were prepared using methods known in the art. HSPC, PEG-DSPE and cholesterol 58% 2% 40%, were dissolved in pure ethanol and heated at 65° C. until full dissolution.

Synthesizing the liposomes: Liposomes contain lipid composition of 58% mol to hydrogenated soybean phosphatidylcholine (HSPC), Mw 762.1; 2 mol % polyethyleneglycol distearoyl-phosphoethanolamine (m2000PEG DSPE)—its role is to reduce aggregation/fusion of liposomes due to steric effects, Mw 2805.54; and 40 mol % Cholesterol Mw 386.65. Working Concentration of the total lipid is 50 mM in solution. The medium was 10% PBS/5% dextrose in deionized water. First the lipids were dissolved in pure ethanol, warmed to 65° C. and added to 1 ml of the medium (warmed too to the same temperature). After direct injection and pipetting, more medium was added to reach the final lipid concentration. Hydrogenated soybean phosphatidylcholine was contributed from Lipoid (Ludwigshafen, Germany); m2000PEG-DSPE was purchased from Avanti (Alabaster, Ala., USA) and Cholesterol (Catalog Number: C8667-500MG) from Sigma (Rehovot, Israel).

DNA Encapsulation: 25 nanaomoles and desalted ssDNA oligos were purchased from Sigma & IDT (Leuven Belgium) with the length range of 50-120 base pairs. After annealing of the two ssDNA, the stock was diluted to 100 μM and was divided to aliquots of 100 micro-liters (μl). For 5 ml of lipid solution, 300 μl of dsDNA was added to the 1 ml medium solution before adding the dissolved lipids (For 3 ml-150 μl of dsDNA). After encapsulation, extruder was used to produce 200 nm liposomes.

Extrusion process: The lipid solution was extruded 3 times through 400 nm and 200 nm membrane. The extruder temperature was set to 65 degrees C. (° C.).

Particle Size Determination via DLS (Dynamic Light Scattering)—After extrusion, size determination was done by DLS (ZetaSizer—ZSP). PDI range was between 0.003-0.08.

In vitro transfection: In vitro experiments were conducted on both B-16 (melanoma) and 4T1 (breast cancer) mouse cancer cells in 8/3.5 cm tissue culture plate. Cells were cultured in RPMI (biological industries), after 24 hours 10% (v/v) of liposome solution was added with fresh medium to the cell culture. Cells were incubated at 37° C. for 24 hours and then analyzed.

DNA Extraction: The medium with the remaining liposomes was discarded and the cells were washed three times with PBSX1 (Biological Industries). The cells were disconnected from the plate with trypsin and transferred into 1.5 ml Eppendorf tubes. Cells were centrifuged at 1200 rpm for 7 min and trypsin was discarded. DNA extraction was conducted using Bligh and Dyer assay; addition of 167 μl 1:2 Chloroform: methanol (v/v), 55.5 μl of chloroform, and 100 μl of deionized water. After centrifugation at 1000 rpm for 5 min, the upper aqueous phase was collected.

DNA Amplification: The dsDNA was amplified in thermo cycler ("Daniel Biotech") using ready mix ("Ornat") in 50 μl reaction. After PCR, the solution was loaded to 3% (w/w) agarose gel ("Hy-Labs") and ran for 25 min.

RT-PCR: Following DNA extraction, the strands were amplified and analyzed using TaqMan Probe in RT-PCR thermo cycler ("Bio Rad").

Cell Sorting: 15 ml of cell suspension with the concentration of $10^6$/ml was taken to flow activated cell sorter (FACS—ARIA). After gating the cells, they were sorted to 1,000 cells, 100, 10 cells and single cell. All the cells were sorted into conic transparent 96 wells from polypropylene. Following the sorting, B&D and PCR were conducted.

Cell Dilutions: Cells were suspended in 1ml medium and counted. The next stage is series of dilutions up to $10^3$ cells-100 μl in 900 μl of PBSX1. Each dilution is diluted again by 10 in order to get $10^3$, $10^2$ and 10 cells: 10 μl to 90 μl deionized water. Finally, in order to get theoretically a single cell, taking a 1 μl from 100 cells dilution into 99 μl of PBSX1.

Confocal/Cell observer: DNA Encapsulation—liposomes containing FAM conjugated DNA, were prepared using the method described above. The liposomes were dialyzed for 24 hours against 10% PBS (membrane type). Fluorescence of samples (triplicates) before and after dialysis, were measured with DLS (manufacture) excitation and emission 566-345 nm respectively. Fluorescence values for after and before dialysis were subdivided to give the encapsulation percentage.

In vivo transfection: 100 μl of $10^6$cells/ml of 4T1 (breast cancer) was injected subcutaneous to 10 weeks balb/c female mice. About 14 weeks later (when the primary tumor was massive enough), 100 μl of liposome solution was injected intravenous. 36 hrs later, the mouse was sacrificed and its organs (+tumor) were taken in ice for further steps.

Example 1

Nanoparticle Fabrication and Labeling

Nanoparticles will be fabricated of lipids using an in-line microfluidic setup (Jahn, A., et al. 2007, *Langmuir* 23, 6289-6293) adapted to accommodate high-throughput synthesis and labeling of the particles (FIG. 2). Particles of appropriate sizes to accommodate the therapeutic payload are fabricated. Chemical agents are loaded into stable HSPC particles (Schroeder, A. et al. 2007, *Langmuir* 23, 4019-4025) and biological therapeutics (e.g., protein/RNA) are synthesized inside ~200 nm 'protein producing nanoparticles'. Recently developed is a synthetic nanoparticles that can be controllably triggered to synthesize proteins and RNA at a target site (Schroeder, A. et al. 2012, *Nano Lett* 12, 2685-2689). These nanoparticles consist of lipid vesicles filled with the molecular machinery responsible for transcription and translation, including amino acids, ribosomes, and DNA caged with a photo-labile protecting group. The particles serve as nano-factories capable of producing RNA/proteins. In vitro and in vivo, protein/RNA synthesis is spatially and temporally controllable, and can be initiated by illuminating micron-scale tissue regions on the timescale of milliseconds. We will use this platform to screen RNA and proteins for their anti-cancer activity.

Figure 3A:
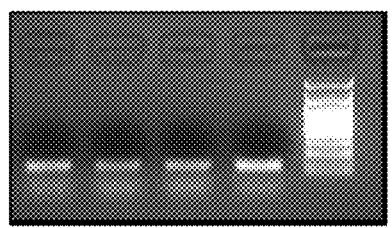
FIGS. 3A-F. Barcoded nanoparticles in malignant cells. DNA barcodes were detected inside clusters of 1,000 (A), 500 (B), 5 (C) cells, and even inside single cells (D). Barcodes can be of various lengths—50, 85, and 120 bp (E)
Figure 3B:
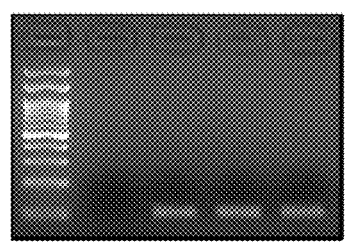
Figure 3C:
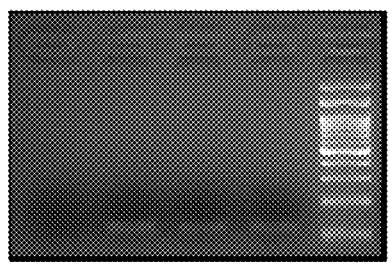
Figure 3D:
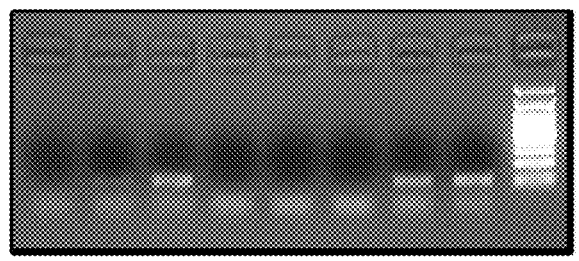
Figure 3E:
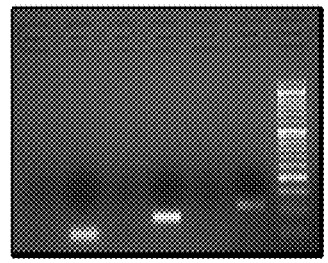
Figure 3F:
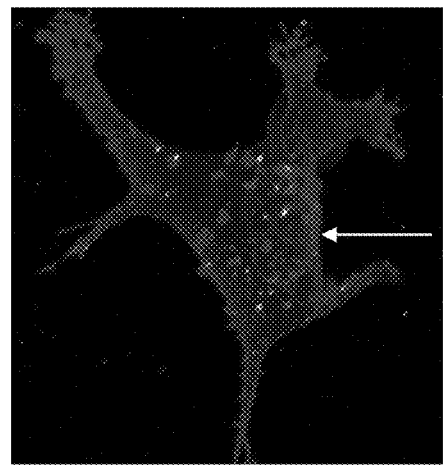

Primary and metastatic therapeutic activity can be modeled in vitro and in vivo. To screen multiple drugs simultaneously nanoparticles are tagged with DNA barcodes (FIG. 3). As seen in FIG. 3, DNA barcodes were detected inside clusters of 1,000 (FIG. 3A), 500 (FIG. 3B), 5 (FIG. 3C) cells, and even inside single cells (FIG. 3D).

Example 2

Assaying Primary and Metastatic Models

Initial in vivo studies were carried out using 4T1 breast cancer models in BALB/c mice (FIG. 4), reported by Weinberg and coworkers. To confirm the clinical accuracy of these models, the bio-distribution and activity of the theranostic nanoparticles was also tested in human derived tumors established in human Embryonic Stem Cell (hESC) teratoma. These tumors are considered to mirror the clinical scenario in an accurate manner including the microenvironment, intratumoral morphologic heterogeneity, cancer cell subpopulations and cellular phenotypes (Burgos-Ojeda, D. et al. 2013, *Cancer Res* 73, 3555-3565, 2845).

First, in order to examine the efficiency of delivery of the barcodes using liposomes, mice were administered with either liposomes containing barcode or naked barcode. 48 hours after injection, the tumors were harvested, homogenized and the barcodes were extracted and amplified. The basal amplification represents unspecific amplification of the barcode in RT-PCR. The amount of barcodes detected in the tumor tissue was significantly greater using the carrier (liposome) (FIG. 5). Since both the DNA strands (barcodes) and the cell membrane are negative charged, DNA doesn't enter the cell without a mediator. Therefore, the presence of the free barcode in the tumor may be explained by DNA strands that reached the extra cellular matrix of the tumor rather than the cells.

Barcoded nanoparticles having a diameter of 100 nanometers and barcoded nanoparticles having a diameter of micron were intravenously injected to BALB/C mice bearing breast cancer tumors. 48 hours after the injection, the tumor was dissociated into single cell suspension and the cells were collected using FACS. The DNA barcodes were extracted and amplified by RT-PCR. Results demonstrate that the uptake of the nanometric nanoparticles was significantly higher than the uptake of the micron scale nanoparticles (FIG. 6). These results suggest that the uptake of the liposomes is size dependent, with preference to the smaller particles.

The first trial of the technology in vivo was by using Doxorubicin (DOX) as a drug model against breast cancer. To determine if there is any difference in the barcode distribution between the barcoded nanoparticles (BNPs) that contain DOX and placebo BNPs that contained barcode only and no drug, the procedure included synthesizing barcoded liposomes in two batches: 1. Liposomes contain barcode only, 2. Liposomes contain barcode and DOX. The barcode was encapsulated in a passive manner while DOX was encapsulated in an active manner. The placebo BNPs were injected separately to one group of mice (n=3), and the DOX BNPs to another groups. 48 hours after injection, the tumor was extracted and dissociated into single cell suspension. The cells were stained with viability dye (7AAD) and sorted in FACS to Live/Dead cells. The barcode was extracted from each group. After the extraction, the DNA barcode was amplified by RT-PCR. The barcode concentration of each group (Live/Dead) was transformed to amount of barcode and normalized in cells amount to get DNA barcode molecules per cell. FIG. 7(A) shows that in the placebo barcoded NPs accumulated mainly in the live cells. This result fits the hypothesis that in dead cells almost no uptake occurs. The second group of the DOX treatment showed preferential distribution in the dead cells (FIG. 7(B)).

Ovarian cancer is prevalent in society with few efficacious therapeutic modalities. The disease is many times detected after metastasizing to the liver or the abdominal space.

In the present study, ovarian tumors are expanded in hESC teratomas in SCID/beige mice, as previously described (Burgos-Ojeda, ibid.). Barcoded nanoparticles loaded with anti-cancer drugs are administered intravenously. Evaluation of the therapeutic task of the nanoparticle is evaluated after 48 hours which enables accumulation in the tumor and carrying out a therapeutic task. The 48 hours timeline has been validated by using 4T1 cells (see, FIG. 8). Post-mortem histological evaluation of the tissue is used to study the tumor bio-distribution. A biopsy sample is then dissociated into a single-cell suspension and the cells are sorted, using antibodies, according to cell subpopulation (including, CD45, CD11B, F4/80, CD13, REST) and viability (live/dead).

Barcoded nanoparticles containing five different drugs or control compounds (FIG. 8 depicts Placebo, Caffeine, Cisplatin, Doxorubicin and Gemcitabine), were injected simultaneously intravenously to BALB/c mice bearing a primary tumor in the hind thigh. 48 hours later, a biopsy was taken from the tumor. The biopsy tissue was then dissociated into a single-cell suspension, and the cells were screened according to their viability (live/dead). Elevated levels of the drug (gemcitabine, cisplatin) barcodes were found in the dead cells in comparison to the live cells. The neutral compound, caffeine, had similar barcode levels in both live and dead cells. As indicated by FIGS. 8A-E, Gemcitabine is more effective than cisplatin for treating this tumor.

The results show a unique distribution for each barcode. Both DOX and Cisplatin showed a clear therapeutic effect as expected. Caffeine showed almost no effect and its distribution was divided almost equally between the dead and the live cells (FIGS. 8A-E). The most astonishing results came from the two sides of the therapeutic scale: the placebo and gemcitabine. Gemcitabine was found the most efficient drug based on its distribution. Almost all the gemcitabine barcodes were accumulated in the dead cells, 6,000 more compare to the live cells (FIG. 8(E)). In the other scale of the therapeutic efficacy, the placebo BNPs were accumulated almost only in the living cells—10,000 more compare to the dead cells, FIG. 8(A). This data suggests that as long as the cell is alive, placebo BNPs will keep accumulating in the cell. This shifts the distribution strongly to the live cells.

This example illustrate a theranostic platform for determining the cell-specific potency of drugs (FIG. 8F), prior to beginning a treatment cycle, as well as studying the therapeutic profile of different drugs within the tumor microenvironment.

Figure 9C:
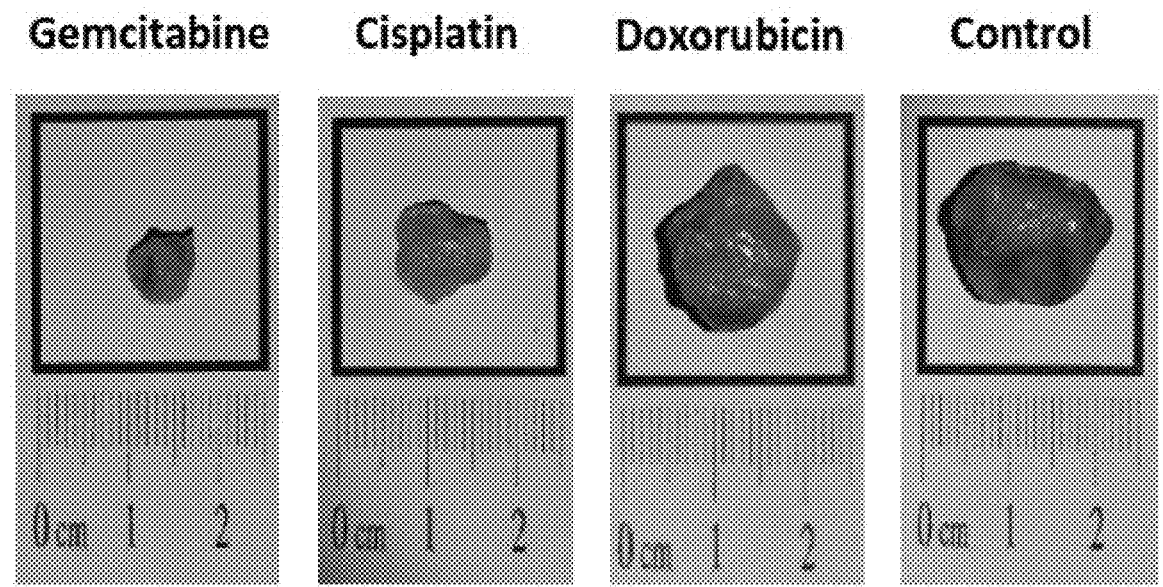
Figure 9D:
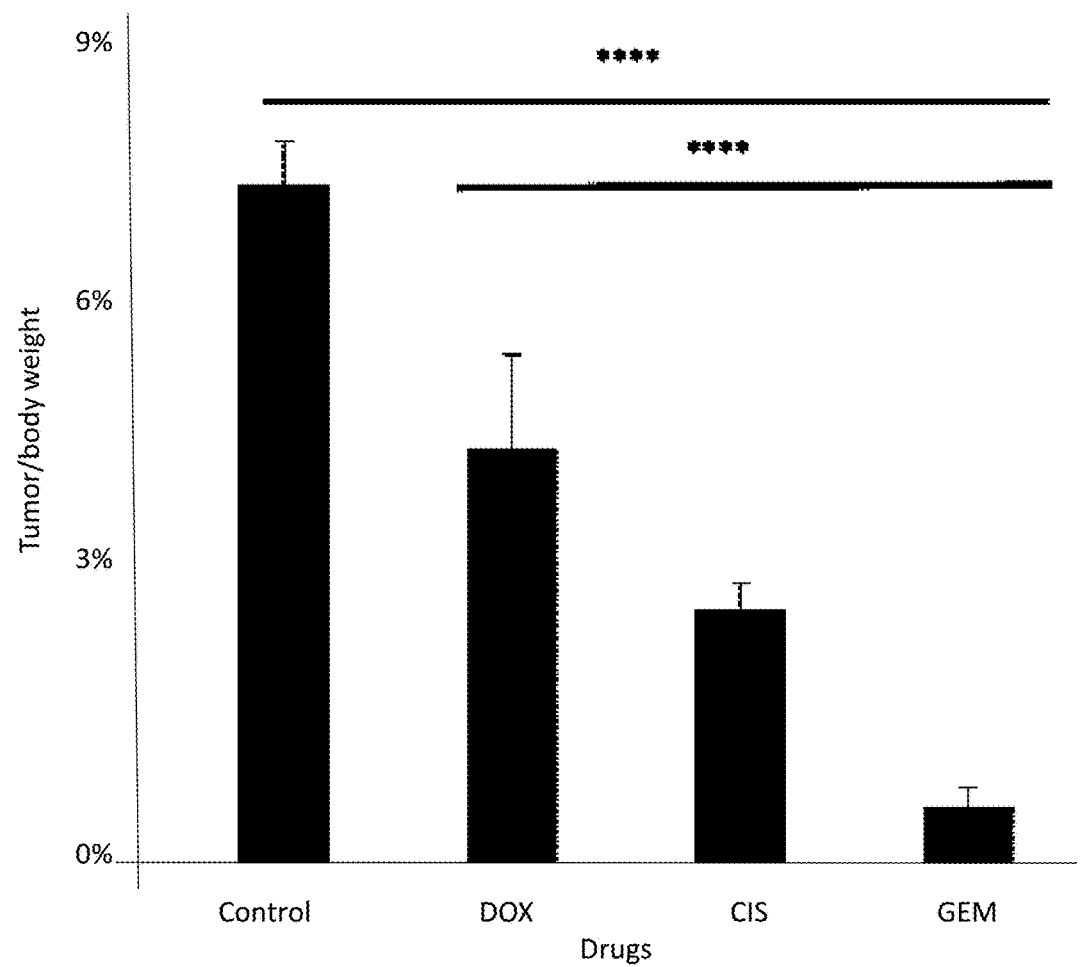

To validate the barcoding analysis of the three chemotherapeutic drugs—Doxorubicin, Cisplatin and Gemcitabine, therapeutic treatment was conducted. The experiment included 4 groups, each containing 6 mice. Each group was treated with single drug for 24 days, starting 10 days post tumor induction. Each dose was given intravenous once a week. Each group was treated with either 5 mg/kg of Doxorubicin, 6 mg/kg of Cisplatin, 125 mg/kg of Gemcitabine or 100 µl of saline as a control. Tumors volumes were measured with caliper and calculated as length/2*(width)$^2$. By looking at FIG. 9(A), the drugs potency can be rated directly based on the differences in the tumor volume change percentage. These results strengthen the diagnostic analysis that rated Gemcitabine as the most efficient drug out of the three drugs. Gemcitabine significantly attenuated the growth of the tumors relative to Doxorubicin, and the control treatments. No clinical toxicity was observed during the period of the experiment. 24 days after starting the treatment, the tumor of each mouse was extracted for further analysis. FIG. 9(B) shows typical tumors from each group. This visualization of the tumor also strengthen the diagnostic results and demonstrate the differences between each treatment. Another indication that strengthen the results is the tumor/body weight ratio. The less the tumor weighs and the more the body weighs, the more effective the drug is. In FIG. 9(C) there is a trend that leads to minimum tumor/body weight ratio in Gemcitabine. The trend correlates to both tumor dimensions and the change in the tumor volume. The tumor weight parameter reflects the effectiveness of the drug to inhibit and damage the tumor growth. The body weight parameter reflects the influence of the drug on the body or how severe are the side effects of the drug. Combining these parameters, can facilitate in determining, which drug is the most effective drug to treat the tumor, and which drug exhibits less toxicity to the body. To check differences in the tissue level between the different groups, all the tumors were studied histologically. Tissue slides from the tumors were stained with hematoxylin and eosin. Microscopic examination of the slides demonstrates highly cellular solid tumors. Interestingly, tumors that showed clinical response to therapy were less cellular and had lower mitotic counts. Additionally, tissue slides were immunohistochemically stained with rabbit monoclonal anti-Ki67 antibody (SP6; Thermo Scientific, Fremont, Calif.) to determine proliferation index (not shown). Analysis of the slides demonstrated lower proliferation index in tumors that received more effective therapy with proliferation index of 85%, 90%, 65% and 40% in control, Doxorubicin, Cisplatin and Gemcitabine treated tumors, respectively.

Example 3

Feasibility of the Process

In vivo experiments showed that using barcode concentration lower than 2 µM resulted in prevention of detection (under the LOD of the systems). The concentration of the particles used for the in vitro studies was hundredth of the concertation of the particles used for the in vivo studies, to prevent overflowing of the particles inside the single layer of the cells. This allows good statistics and robust analysis. Analysis of the encapsulated barcodes showed that the sufficient range of barcode molecules inside the particle should range between 5-100 barcode molecules/particle (this was calculated based on the DNA to lipid molar ratio). For statistical analysis of the results, it was found that the efficient particles concertation has a range of 2-20 µM. When using a concentration lower than 2 µM, there is high possibility that not all the cells will contain at least one particle. Above this concertation, the SNR (signal to noise ratio) in the system will be too low.

In order to determine the optimal time point for harvesting the cells post administration of the particles, the time for particles accumulation in the tissue, the time it takes the drug to kill the cell, and the time it takes the barcode to be degraded in the cell, should all be taken into account. Taking these parameters into account, circulation period of time of the particles, before harvesting them by performing a biopsy, was optimized to 48 hours.

In vivo works in bio-distribution showed that it takes 24 hours to the particles to reach the maximal concertation in the tumor tissue. In addition, in vitro works showed that the average time to reach the maximal therapeutic efficacy of several drugs varies between 24 hours to 48 hours. Taking into considerations the period of time it takes the particles to reach the tissue and the drug to be lethal in the cell—the optimal period of time should be 30-48 hours. Extending this period of time will risk the barcode analysis due to degradation of the barcode by DNases which are present inside the cells.

Example 4

Particles Compositions for Intravenous and Intratumoral Administration

Preferable particles composed of unique lipid constitutes were prepared to suit administration modes, specifically intravenous versus intratumor administration. Exemplary compositions for particles administered intravenously and particles administered intratumoraly are summarized in table 1. Table 1:

| Administration | Composition | | |
|---|---|---|---|
| | Type of lipid | Range (% mol) | Particle Size (nm) |
| Intravenous | Lipid | 40-70 | 5-250 |
| | Cholesterol | 20-40 | |
| | PEG-lipid | 4-8 | |
| | Functional lipid (cationic lipid or a lipid with a targeting moeity) | 0-3 | |
| Intratumor | Lipid | 50-80 | 5-300 |
| | Cholesterol | 0-30 | |
| | PEG-LIPID | 1-3 | |
| | Functional lipid (cationic lipid or a lipid with a targeting moeity) | 4-8 | |

The invention claimed is:

1. A method of determining in vivo biodistribution of a type of carrier in a subject, the method comprising:
   a. systemically administering to said subject a composition comprising a first type of carrier comprising one or more nucleic acid molecules comprising a barcode uniquely identifying said type of carrier;
   b. obtaining from said subject a sample from a plurality of tissue comprising cells; and
   c. identifying, in said cells the presence of said nucleic acid barcode, wherein the presence of said nucleic acid barcode indicates the in vivo biodistribution of said type of carrier to said tissue;
   wherein each of said one or more nucleic acid molecules is 500 or fewer nucleotides in length;
   thereby determining biodistribution of a type of carrier in a subject.

2. The method of claim 1, wherein said method is a method of determining biodistribution of a plurality of types of carriers, and wherein said composition comprises a plurality of types of carriers, wherein each type of carrier comprises one or more nucleic acid barcodes uniquely identifying said type of carrier.

3. The method of claim 2, wherein said types of carriers differ in their composition.

4. The method of claim 3, wherein said types of carriers differ in their lipid composition.

5. The method of claim 1, wherein said carrier is selected from a carrier having a diameter of 5-300 nanometer, a lipid-based particle, a liposome, a carrier comprising a tag and a micelle.

6. The method of claim 5, wherein said carrier comprises a tag and said tag is selected from the group consisting of a fluorophore, a chromophore, a chemiluminescent molecule, a magnetic particle, a dye, a metal, a rare earth, a metal and a radioactive isotope.

7. The method of claim 1, wherein said carrier is a lipid-based particle.

8. The method of claim 7, wherein said carrier is devoid of a cationic surfactant.

9. The method of claim 1, wherein said obtaining is performed from 24-72 hours following said administration.

10. The method of claim 1, further comprising a step of sequencing said nucleic acid barcode.

11. The method of claim 1, further comprising a step of amplifying said nucleic acid barcode.

12. The method of claim 1, wherein said sample is disassembled into a single-cell suspension prior to step (c).

13. The method of claim 1, wherein said type of carrier further comprises a tag and wherein cells of said sample are sorted using a method selected from the group consisting of: FACS, magnetic bead sorting, microfluidic based sorting, cell-tension based sorting, and ELISA.

14. The method of claim 13, wherein said tag is selected from the group consisting of a fluorophore, a chromophore, a chemilluminescent molecule, a magnetic particle, a dye, a metal, a rare earth, a metal and a radioactive isotope.

15. The method of claim 1, wherein each of said one or more nucleic acid barcodes comprises a sequence which is not substantially identical or complementary to a nucleic acid of a cell of said subject.

16. The method of claim 1, wherein said carriers further comprises a therapeutic agent.

17. The method of claim 7, wherein said lipid-based particle is a liposome or a micelle.

18. The method of claim 1, wherein said systemically administering is intravenously administering.

19. The method of claim 1, wherein said in vivo biodistribution is bodily biodistribution.

20. A method of determining in vivo bodily biodistribution of a type of carrier in a subject, the method comprising:
   a. systemically administering to said subject a composition comprising a first type of carrier comprising one or more nucleic acid molecules comprising a barcode uniquely identifying said type of carrier;
   b. obtaining from said subject a sample from a plurality of tissues comprising cells; and
   c. identifying, in said cells the presence of said nucleic acid barcode, wherein the presence of said nucleic acid barcode indicates the in vivo bodily biodistribution of said type of carrier to said tissues;
   wherein each of said one or more nucleic acid molecules is 500 or fewer nucleotides in length;
   thereby determining in vivo bodily biodistribution of a type of carrier in a subject.

* * * * *